United States Patent
Tshuva et al.

(10) Patent No.: US 10,017,533 B2
(45) Date of Patent: Jul. 10, 2018

(54) CYTOTOXIC TITANIUM AND VANADIUM COMPLEXES

(71) Applicant: YISSUM RESEARCH DEVELOPMENT COMPANY OF THE HEBREW UNIVERSITY OF JERUSALEM LTD., Givat Ram, Jerusalem (IL)

(72) Inventors: Edit Tshuva, Rehovot (IL); Jacob Hochman, Jerusalem (IL)

(73) Assignee: YISSUM RESEARCH DEVELOPMENT COMPANY OF THE HEBREW UNIVERSITY OF JERUSALEM LTD., Jerusalem (IL)

(*) Notice: Subject to any disclaimer, the term of this patent is extended or adjusted under 35 U.S.C. 154(b) by 0 days.

(21) Appl. No.: 14/421,258

(22) PCT Filed: Aug. 15, 2013

(86) PCT No.: PCT/IL2013/050698
§ 371 (c)(1),
(2) Date: Feb. 12, 2015

(87) PCT Pub. No.: WO2014/027355
PCT Pub. Date: Feb. 20, 2014

(65) Prior Publication Data
US 2015/0329578 A1    Nov. 19, 2015

Related U.S. Application Data

(60) Provisional application No. 61/683,258, filed on Aug. 15, 2012.

(51) Int. Cl.
*C07F 17/00* (2006.01)
*C07F 7/28* (2006.01)
*C07F 9/00* (2006.01)

(52) U.S. Cl.
CPC ............ *C07F 17/00* (2013.01); *C07F 7/28* (2013.01); *C07F 9/005* (2013.01)

(58) Field of Classification Search
None
See application file for complete search history.

(56) References Cited

FOREIGN PATENT DOCUMENTS

WO    2007/128968 A1    11/2007
WO    2012/007948 A2     1/2012

OTHER PUBLICATIONS

Tinoco et al (J Am Chem Soc 129:3444-3454, 2007).*
CAS RN 374566-86-6 (entered into STN Dec. 7, 2001).*
CAS RN 1633360-08-5 (entered into STN May 26, 1995).*
Boyle et al (Inorganic Chemistry, 48:9191-9204, 2009).*
STN Accession No. 2009:1119852.*
Manna, C. et al. "Unexpected Influence of Stereochemistry on the Cytotoxicity of Highly Efficient TiIV Salan Complexes: New Mechanistic Insights." Chem. Eur. J. 2011, 17, 14094-14103.
Manna, C. et al. "New Insights on the Active Species and Mechanism of Cytotoxicity of Salan-Ti(IV) Complexes: A Stereochemical Study." Inorg. Chem. 2011, 50, 10284-10291.
Manna, C. et al. "Cytotoxic Salan-Titanium(IV) Complexes: High Activity Toward a Range of Sensitive and Drug-Resistant Cell Lines, and Mechanistic Insights." Chem Med. Chem. 2012, 7, 703. 2012 Wiley-VCH Verlag GmbH& Co. KGaA, Weinheim.
Manna, C. et al. "Markedly different cytotoxicity of the two enantiomers of C2-symmetrical Ti(IV) phenolato complexes; mechanistic implications." Received Jun. 29, 2009, Accepted Oct. 16, 2009. First published as an Advance Article on the web Nov. 2, 2009. DOI: 10.1039/b920786b. Dalton Trans., 2010, 39, 1182-1184.
Meker et al. "Major impact of N-methylation on cytotoxicity and hydrolysis of salan Ti(IV) complexes: sterics and electronics are intertwined." Received Jun. 13, 2011, Accepted Aug. 3, 2011. DOI: 10.1039/c1dt11081. Dalton Trans, vol. 40, pp. 9802-9809.
Peri et al. "Different ortho and para Electronic Effects on Hydrolysis and Cytotoxicity of Diamino Bis(Phenolato) "Salan" Ti(IV) Complexes." Institute of Chemistry, The Hebrew University of Jerusalem, 91904, Jerusalem, Israel. Inorg. Chem. 2011, 50, 1030-1038. DOI: 10.1021/ic101693v. Received Aug. 19, 2010.
Peri et al. "Synthesis, Characterization, Cytotoxicity, and Hydrolytic Behavior of C2- and C1-Symmetrical TiIV Complexes of Tetradentate Diamine Bis(Phenolato) Ligands: A New Class of Antitumor Agents." Chem. Eur. J. 2009, 15, 2403-2415. 2009 Wiley-VCH Verlag GmbH&Co. KGaA, Weinheim. DOI: 10.1002/chem.200801310.
Shavit et al. "Active Cytotoxic Reagents Based on Non-metallocene Non-diketonato Well-Defined C2-Symmetrical Titanium Complexes of Tetradentate Bis(phenolato) Ligands." Department of Inorganic Chemistry, The Hebrew University of Jerusalem, 91904, Jerusalem, Israel. Received Jul. 17, 2007; Published on Web Sep. 18, 2007. J. Am. Chem. Soc. 2007, 129, 12098-12099.
Tshuva et al. "Cytotoxic Titanium(IV) Complexes: Renaissance." Eur. J. Inorg. Chem. 2009, 2203-2218. 2009 Wiley-VCH Verlag GmbH & Co. KGaA, Weinheim. DOI: 10.1002/ejic.200900198.
Tshuva et al. "Modern cytotoxic titanium(IV) complexes; Insights on the enigmatic involvement of hydrolysis." Institute of Chemistry, The Hebrew University of Jerusalem, Givat Ram Campus, 91904 Jerusalem, Israel. Coordination Chemistry Reviews 253 (2009) 2098-2115. 2008 Elsevier B.V. doi:10.1016/j.ccr.2008.11.015.
Glasner et al. "A Marked Synergistic Effect in Antitumor Activity of Salan Titanium(IV) Complexes Bearing Two Differently Substituted Aromatic Rings." Institute of Chemistry, The Hebrew University of Jerusalem, Jerusalem, 91904 Israel. dx.doi.org/10.1021/ja208219f | J. Am. Chem. Soc. 2011, 133, 16812-16814. 2011 American Chemical Society.

(Continued)

*Primary Examiner* — Craig D Ricci
(74) *Attorney, Agent, or Firm* — Oliff PLC

(57) ABSTRACT

The present application provides a family of highly resistant and water-stable Titanium and Vanadium complexes, which may be administered directly without a further hydrolysis step and which solubility and cell-penetration characteristics may be modifiable by reducing their particle size to the nanoscale.

2 Claims, 5 Drawing Sheets

(56) References Cited

OTHER PUBLICATIONS

Tinoco et al. "Cytotoxicity of a Ti(IV) compound is independent of serum proteins." Department of Chemistry and Chemical Biology, Harvard University, Cambridge MA 02138; and Department of Chemistry, Yale University, New Haven CT 06520. Edited by Harry B. Gray, California Institute of Technology, Pasadena, CA, and approved Feb. 14, 2012 (received for review Nov. 22, 2011) 5016-5021 PNAS Mar. 27, 2012 vol. 109 No. 13.

Immel et al. "Highly Selective Apoptotic Cell Death Induced by Halo-Salane Titanium Complexes." ChemMedChem 2009, 4, 738-741. 2009 Wiley-VCH Verlag GmbH& Co. KGaA, Weinheim. DOI: 10.1002/cmdc.200900038.

Immel et al. "Cytotoxic Titanium Salan Complexes: Surprising Interaction of Salan and Alkoxy Ligands." Chem. Eur. J. 2010, 16, 2775-2789. 2010 Wiley-VCH Verlag GmbH&Co. KGaA, Weinheim. DOI: 10.1002/chem.200902312.

Immel et al. "Synthesis and X-ray structure analysis of a heptacoordinate titanium(IV)-bis-chelate with enhanced in vivo antitumor efficacy." Chem. Commun., 2012, 48, 5790-5792. Received Mar. 4, 2012, Accepted Apr. 16, 2012. DOI: 10.1039/c2cc31624b.

Noyes et al. "The Rate of Solution of Solid Substances in their own Solutions." pp: 930-934. J Am Chem Soc.

Knapp "The Solubility of Small Particles and the Stability of Colloids." 1921 pp: 457-465.

Simonelli et al. "Inhibition of Sulfathiazole Crystal Growth by Polyvinylpyrrolidone." vol. 59, No. 5, May 1970. pp: 633-638. Journal of Pharmacuetical Sciences.

Margulis-Goshen. "Formation of organic nanoparticles from volatile microemulsions." Institute of Chemistry, The Hebrew University of Jerusalem, Jerusalem 91904, Israel. Chemistry Department and the Lise Meitner-Minerva Center of Computational Quantum Chemistry, Bar-Ilan University, Ramat-Gan, Israel. Technische Universität Berlin, Stranski-Laboratorium für Physikalische and Theoretische Chemie, Institut für Chemie, Berlin, Germany. Journal of Colloid and Interface Science 342 (2010) 283-292.

Margulis-Goshen. "Formation of solid organic nanoparticles from a volatile catanionic microemulsion." Soft Matter, 2011, 7, 9359-9365. Received Apr. 9, 2011, Accepted Jul. 22, 2011. DOI: 10.1039/c1sm05637a.

Margulis-Goshen. "Formation of celecoxib nanoparticles from volatile microemulsions." Pharmaceutical Nanotechnology. Casali Institute of Applied Chemistry, Institute of Chemistry, The Hebrew University of Jerusalem, Jerusalem, Israel. Department of Biotechnology and Food Engineering, Technion Israel Institute of Technology, Haifa, Israel. Russell Berrie Nanotechnology Institute, Technion Israel Institute of Technology, Haifa, Israel. International Journal of Pharmeceutics 393. pp. 230-237. 2010 Elsevier B.V.

Margulis-Goshen. "Formation of simvastatin nanoparticles from microemulsion." Original Article: Engineering Nanomedicine, Pharmacology, Formulation. Institute of Chemistry, Casali Institute of Applied Chemistry, The Hebrew University of Jerusalem, Jerusalem, Israel. Received Aug. 24, 2008; accepted Nov. 20, 2008. Nanomedicine: Nanotechnology, Biology, and Medicine 5 (2009) 274-281. 2009 Elsevier Inc.

Immel et al. "Cytotoxic dinuclear titanium-salan complexes: Structural and biological characterization." Fachbereich Chemie and Konstanz Research School Chemical Biology, Universität Konstanz, Universitätsstraße 10, Fach 720, 78457 Konstanz, Germany. 2011 Elsevier Inc. Journal of Inorganic Biochemistry 106 (2012) 68-75.

Caruso et al. "Synthesis, Structure, and Antitumor Activity of a Novel Tetranuclear Titanium Complex." J. Med. Chem. 2000, 43, 3665-3670. Received Oct. 28, 1999. 2000 American Chemical Society.

Higham et al. "Multidentate aminophenol ligands prepared with Mannich condensations." Tetrahedron Letters 47 (2006) 4419-4423. Department of Chemistry, College of the Holy Cross, Worcester, MA 01610, USA Department of Chemistry, University of Akron, Akron, OH 44325, USA; Received Mar. 21, 2006; revised Apr. 12, 2006; accepted Apr. 14, 2006. 2006 Elsevier Ltd.

Reytman et al. "Highly cytotoxic vanadium(V) complexes of salan ligands; insights on the role of hydrolysis." Received Aug. 11, 2011, Accepted Feb. 7, 2012; DOI: 10.1039/c2dt11514j. Dalton Trans., 2012, 41, 5241-5247.

Xie et. al. "Syntheses, structure and magnetic properties of hexanuclear MnIII 2MIII4 (M=Y, Gd, Td, Dy) complexes." Dalton Trans., 2012, 41, 10589-10595.

Schmitt et al. "Synthesis, Redox Properties, and EPR Spectroscopy of Manganese(III) Complexes of the Ligand N,N-Bis(2-hydroxybenzyl)-N'-2-hydroxybenzylidene-1,2-diaminoethane: Formation of Mononuclear, Dinuclear, and Even Higher Nuclearity Complexes." Chem Eur. J. 2002, 8, No. 16. pp. 3757-3768. 2002 Wiley-VCH Verlag GmbH & Co. KGaA, Weinheim.

Chandrasekaran et al. "A New Class of Silatranes: Structure and Dynamic NMR Behavior." Contribution from the Department of Chemistry, LGRT 701, Box 34510, University of Massachusetts, Amherst, Massachusetts 01003-4510. Received Jul. 26, 1999. J. Am. Chem. Soc. 2000, 122, 1066-1072. 2000 American Chemical Society.

Whiteoak et al. "Electronic effects in oxo transfer reactions catalysed by salem molybdenum (VI) cis-dioxo complexes." Received Nov. 21, 2008, Accepted Jan. 9, 2009. Dalton Trans, 2009, 2337-2344. DOI: 10.1039/b820754b.

Correia et al. "Vanadium (IV and V) complexes of Schiff Bases and Reduced Schiff Bases Derived from the Reaction of Aromatic o-Hydroxyaldehydes and Diamines: Synthesis, Characterisation and Solution Studies." 2005 Wiley-VCH Verlag GmbH & Co. KGaA, Weinheim. Eur. J. Inorg, Chem 2005 732-744. DOI: 10.1002/ejic.200400481.

Meker et al. "High Antitumor Activity of Highly Resistant Salan-Titanium(IV) Complexes in Nanoparticles: An Identified Active Species." 2012 Wiley-VCH Verlag GmbH & Co. KgaA, Weinheim. Angew. Chem. Int. Ed. 2012, 51. XP05511249 vol. 51, pp. 10515-10517.

Kikushima et al. "Vanadium-catalyzed oxidative bromination promoted by Bronsted acid or Lewis acid." Department of Applied Chemistry, Graduate School of Engineering, Osaka University, Yamada-oka, Suita, Osaka 565-0871, Japan. 2010 Elsevier Ltd. XP027173857, Tetrahedron 2010. vol. 66, No. 34, Aug. 21, 2010, pp. 6906-6911.

Mba et al. "C3 Vanadium(V) Amine Triphenolate Complexes: Vanadium Haloperoxidase Structural and Functional Models." XP055112254 Inorganic Chemistry vol. 47, No. 19. 2008 American Chemical Society. pp. 8616-8618.

Groysman et al. "Vanadium(III) and Vanadium(V) Amine Tris(Phenolate) Complexes." XP055112259 Inorganic Chemistry, vol. 44, No. 14 2005, pp. 5073-5080.

Colpas et al. "Preparation of VO3+ and VO2+ Complexes Using Hydrolytically Stable, Asymmetric Ligands Derived from Schiff Base Precursors." XP001098101, Inorg. Chem. vol. 33, No. 21, 1994, pp. 4669-4675.

Meshkini et al. "Chemosensitization of human leukemia K562 cells to taxol by a Vanadium-salen complex." XP027491308, Experimental and Molecular Biology vol. 89, No. 3, 2010, pp. 334-342.

Rosu et al. "Metal-based biologically active agents: Synthesis, characterization, antibacterial and antileukemia activity evaluation of Cu(II), V(IV) and Ni(II) complexes with antipyrine-derived compounds." XP026835705, vol. 45, No. 2, 2010, pp. 774-781. European Journal of Medicinal Chemistry.

* cited by examiner

CYTOTOXIC TITANIUM AND VANADIUM COMPLEXES

TECHNOLOGICAL FIELD

The invention generally relates to compounds, compositions and nanoparticles comprising highly water-resistant titanium and vanadium complexes.

BACKGROUND OF THE INVENTION

Titanium (IV) based anticancer complexes were the first to enter clinical trials following platinum compounds. In particular, budotitane ((bzac)$_2$Ti(OEt)$_2$) and titanocene dichloride (Cp$_2$TiCl$_2$) demonstrated high antitumor activity toward a range of cancer cells; however, these complexes, both containing two labile ligands, were limited by aquatic instability. Therefore, mechanistic aspects remain unresolved, including the nature of the active species and its identification out of the multiple hydrolysis products formed. Vanadium compounds have also been investigated and some derivatives showed high activity. Low stability and rich aqueous chemistry, however, were again limiting factors.

The inventors of the invention have introduced cytotoxic salan Ti (IV) complexes [1-11], which are: (a) substantially more hydrolytically stable than known Ti (IV) complexes; and (b) markedly more active than (bzac)$_2$Ti(OiPr)$_2$, Cp$_2$TiCl$_2$, and cis-platin toward variety of cancer-derived cell lines. Structure activity relationship studies based on both salan and labile ligand variations revealed that reduced steric bulk was favored for cytotoxicity. Additionally, all cytotoxic complexes slowly gave defined oxo-bridged polynuclear hydrolysis products. Direct measurements on the isolated clusters showed no activity.

Additional publications on salan complexes containing labile groups have also been described [12-25].

The inventors have also reported on salan vanadium (V) monoalkoxo compounds, which showed lower stability in water, yet high cytotoxicity [26,32].

REFERENCES

[1] C. M. Manna, G. Armony, E. Y. Tshuva, *Chem. Eur. J.* 2011, 17, 14094,
[2] C. M. Manna, G. Armony, E. Y. Tshuva, *Inorg. Chem.* 2011, 50, 10284,
[3] C. M. Manna, O. Braitbard, E. Weiss, J. Hochman, E. Y. Tshuva, *Chem. Med. Chem.* 2012, 7, 703,
[4] C. M. Manna, E. Y. Tshuva, *Dalton Trans.* 2010, 39, 1182,
[5] S. Meker, C. M. Manna, D. Peri, E. Y. Tshuva, *Dalton Trans.* 2011, 40, 9802,
[6] D. Peri, S. Meker, C. M. Manna, E. Y. Tshuva, *Inorg. Chem.* 2011, 50, 1030,
[7] D. Peri, S. Meker, M. Shavit, E. Y. Tshuva, *Chem. Eur. J.* 2009, 15, 2403,
[8] M. Shavit, D. Peri, C. M. Manna, J. S. Alexander, E. Y. Tshuva, *J. Am. Chem. Soc.* 2007, 129, 12098,
[9] E. Y. Tshuva, J. A. Ashenhurst, *Eur. J. Inorg. Chem.* 2009, 2203,
[10] E. Y. Tshuva, D. Peri, *Coord. Chem. Rev.* 2009, 253, 2098,
[11] H. Glasner, E. Y. Tshuva, *J. Am. Chem. Soc.* 2011, 133, 16812,
[12] A. D. Tinoco, H. R. Thomas, C. D. Incarvito, A. Saghatelian, A. M. Valentine, *Proc. Natl. Acad. Sci. USA* 2012, 109, 5016,
[13] T. A. Immel, M. Debiak, U. Groth, A. Burkle, T. Huhn, *Chem. Med. Chem* 2009, 4, 738,
[14] T. A. Immel, U. Groth, T. Huhn, *Chem. Eur. J.* 2010, 16, 2775,
[15] T. A. Immel, M. Grutzke, A.-K. Spate, U. Groth, P. Ohlschlager, T. Huhn, *Chem. Commun.* 2012, 48, 5790,
[16] A. A. Noyes, W. R Whitney, *J Am Chem Soc* 1987, 19, 930,
[17] L. F. Knapp, *Trans. Faraday Soc* 1922, 17, 457,
[18] A. P. Simonelli, S. C. Mehta, W. I. Higuchi, *J. Pharm. Sci.* 1970, 59, 633,
[19] K. Margulis-Goshen, H. D. Netivi, D. T. Major, M. Gradzielski, U. Raviv, S. Magdassi, *J. Colloid Interface Sci.* 2010, 342, 283,
[20] K. Margulis-Goshen, B. F. B. Silva, E. F. Marques, S. Magdassi, *Soft Matter* 2011, 7, 9359,
[21] K. Margulis-Goshen, E. Kesselman, D. Danino, S. Magdassi, *Int. J. Pharm.* 2010, 393, 230,
[22] K. Margulis-Goshen, S. Magdassi, *Nanomedicine* 2009, 5, 274,
[23] T. A. Immel, M. Grutzke, E. Batrogg, U. Groth, T. Huhn, *J. Inorg. Biochem.* 2012, 106, 68,
[24] F. Caruso, M. Rossi, J. Tanski, R. Sartori, R. Sariego, S. Moya, S. Diez, E. Navarrete, A. Cingolani, F. Marchetti, C. Pettinari, *J. Med. Chem.* 2000, 43, 3665,
[25] C. S. Higham, D. P. Dowling, J. L. Shaw, A. Cetin, C. J. Ziegler, J. A. Farrell, *Tetrahedron Lett.* 2006, 47, 4419,
[26] L. Reytman, O. Braitbard, E. Y. Tshuva, *Dalton Trans.* 2012, 41, 5241,
[27] Q. Xie, A. Cui, J. Taob and H. Kou, *Dalton Trans.*, 2012, 41, 10589,
[28] H. Schmitt, R. Lomoth, A. Magnuson, J. Park, J. Fryxelius, M. Kritikos, J. Martensson, L. Hammarstrom, L. C. Sun, B. Akermark, *Chem. Eur. J.* 2002, 8, 3757,
[29] A. Chandrasekaran, R. O. Day, R. R. Holmes, *J. Am. Chem. Soc.* 2000, 122, 1066,
[30] C. J. Whiteoak, G. J. P. Britovsek, V. C. Gibson, A. J. P. White, *Dalton Trans.* 2009, 2337,
[31] I. Correia, J. C. Pessoa, M. T. Duarte, M. F. M. da Piedade, T. Jackush, T. Kiss, M. Castro, C. Geraldes, F. Avecilla, *Eur. J. Inorg. Chem.* 2005, 732,
[32] International Publication No. WO 2012/007948.

SUMMARY OF THE INVENTION

Herein, the inventors disclose a novel family of isolated compounds which are based on the new understanding that labile ligands are not required for endowing cytotoxicity in titanium (having element symbol Ti) and vanadium (having element symbol V) complexes unlike for cis-platin; cellular penetration, which is size-dependent, and/or impaired solubility, have been found to be limiting factors when inert compounds were investigated.

The present application provides a family of highly resistant and water-stable Titanium and Vanadium complexes, which may be administered directly without a further hydrolysis step and which solubility and cell-penetration characteristics may be modifiable by, e.g., reducing their particle size to the nanoscale. The compounds of the invention have been found superior, in both effectiveness and toxicity to previously prepared Ti and V metal complexes and to cis-platin.

Thus, in one aspect of the present invention, there is provided a metal complex, e.g., wherein the metal is Ti or V, comprising a titanium atom or a vanadium atom covalently bound to a single polydentate ligand and optionally to no more than 1 labile monodentate group or an oxo group (wherein the oxo group =O is bonded to the metal atom), with the proviso that the metal complex is not the compound (based on ligand L63) herein designated compound 63, having the structure:

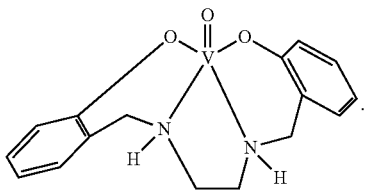

In some embodiments, the metal complexes of the invention are not catalysts.

In some embodiments, the metal complexes of the invention are catalysts in any one chemical transformation. In further embodiments, the metal complexes of the invention are not catalysts in chemical transformations carried out ex-vivo.

In some embodiments, the metal complex comprising water-stable bonds; namely—wherein any bond in the molecule, e.g., between the polydentate ligand and the metal atom, or any bond in the ligand, does not dissociate upon contact with water (in other words, these complexes do not undergo hydrolysis). In some embodiments, the polydentate ligand is free of acid (e.g., carboxylic acid) groups or derivatives thereof (e.g., esters or amides). Thus, in a compound according to the present invention, the compound is not the compound having the following structure [12]:

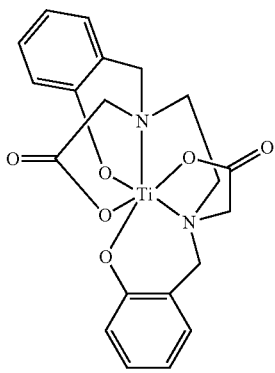

The "polydentate ligand", being a 'donor group', is a ligand having more than one atom that can coordinate (or link, associate) directly to the metal atom in a complex according to the invention. In some embodiments, the polydentate ligand coordinating with the metal atom comprises a plurality of heteroatoms selected from N, O and S, each being capable of forming covalent or coordinative bonds with the metal atom.

In some embodiments, said polydentate ligand comprises 4 or 5 or 6 or 7 heteroatoms. In some embodiments, the ligand is a tetradentate ligand (comprising 4 heteroatoms). In some embodiments, the ligand is a pentadentate ligand (comprising 5 heteroatoms). In other embodiments, said ligand is a hexadentate ligand (comprising 6 heteroatoms).

In some embodiments, the polydentate ligand is a tetradentate or a hexadentate or a pentadentate ligand, having the general structures depicted below, wherein each X denoting the same or different heteroatom (N, O, S):

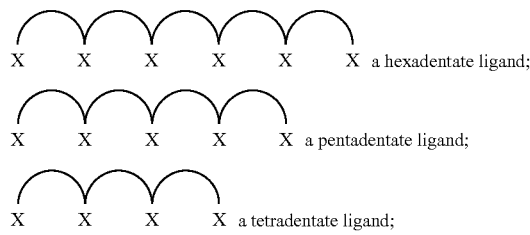

wherein each curved line denotes an atom or a group containing a plurality of atoms bridging (or linking) the heteroatoms (denoted by 'X').

Alternatively, the ligands may be selected from the structures below:

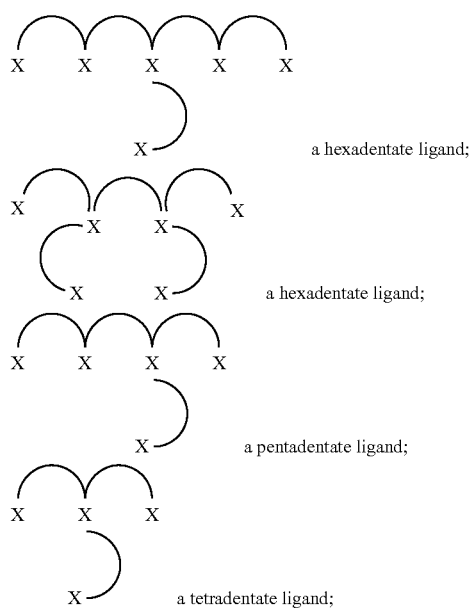

wherein each X being the same or different heteroatom and each curved line being as defined above.

In each of the exemplified ligands above, each X atoms being associated with the metal atom via covalent or coordinative bonding.

In some embodiments, the metal atom is bound to the polydentate ligand through at least three covalent bonds.

In some embodiments, the polydentate ligand comprises a plurality of heteroatoms and at least one phenol group (herein referred to as a 'phenolato group').

In some embodiments, the polydentate ligand comprises a plurality of oxygen and nitrogen atoms; one of said oxygen atoms being bonded to a phenyl ring (forming a phenolato group).

In some embodiments, the polydentate ligand being selected from ligands designated herein L1 through L71:

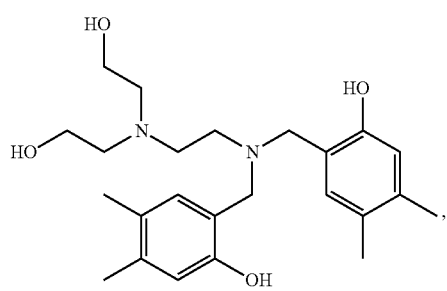
L1
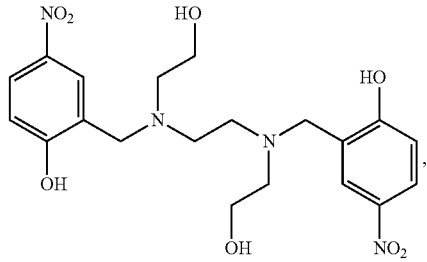
L6
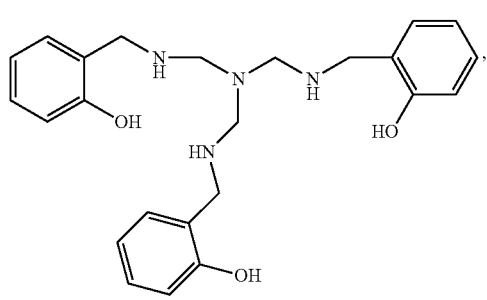
L2
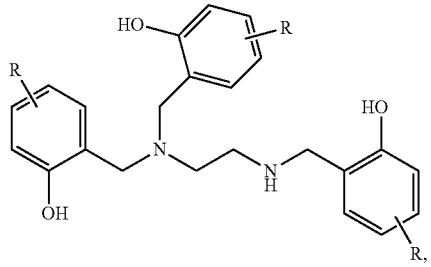
L7
wherein each R=H,
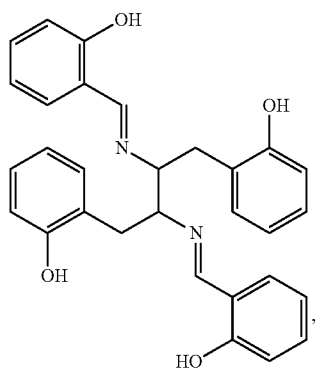
L3
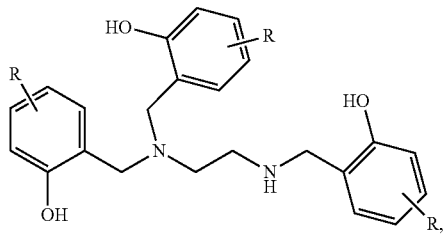
L8
wherein each R=p-Me,
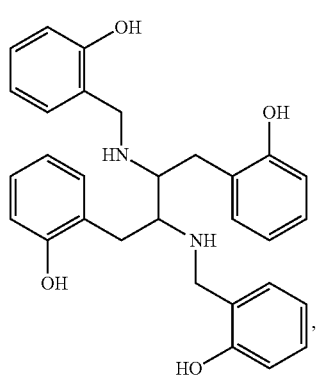
L4
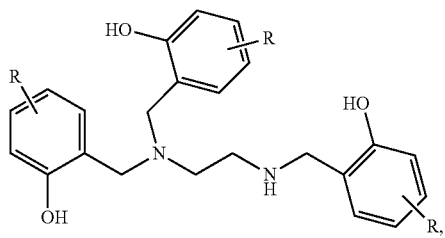
L9
wherein each R=p-Cl,
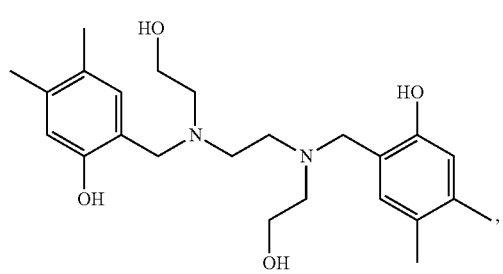
L5
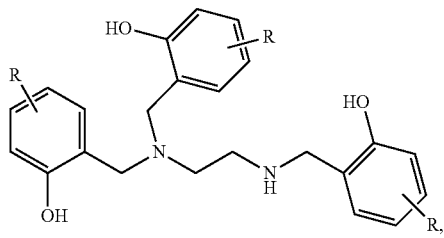
L10
wherein each R=p-O-Me,

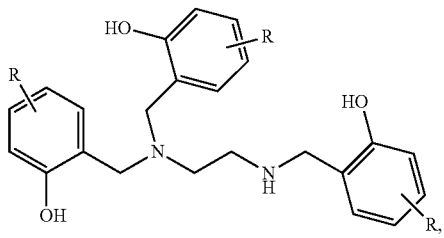
L11
wherein each R=p-O-tBu,
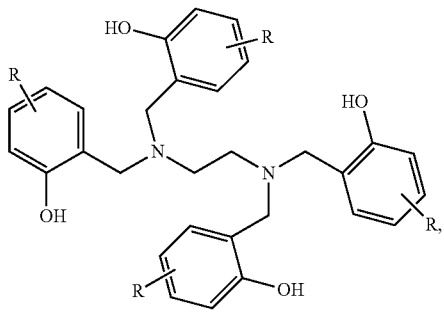
L12
wherein each R=p-Me,
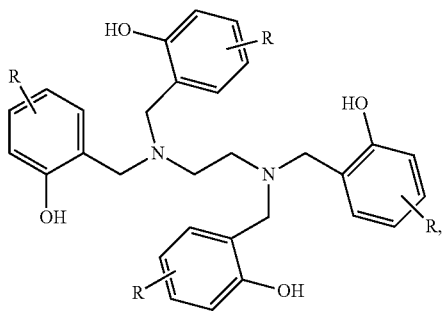
L13
wherein each R=m,p-Me,
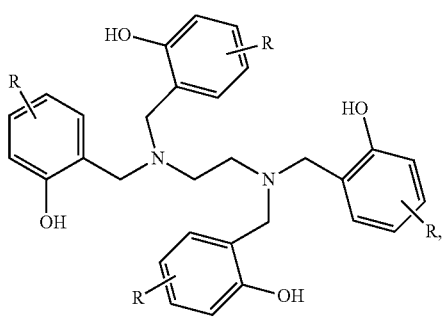
L14
wherein each R=H,
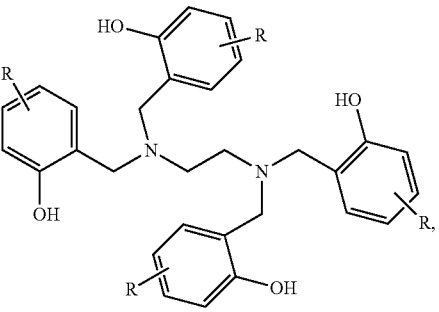
L15
wherein each R represents a halide atom (Cl, Br, I or F), substituted para- to the hydroxyl groups or ortho- and para- to the hydroxyl group,
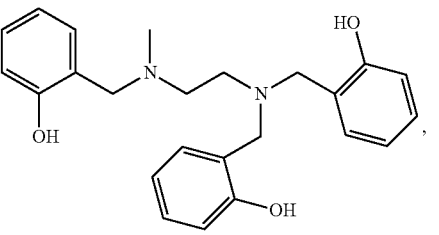
L16
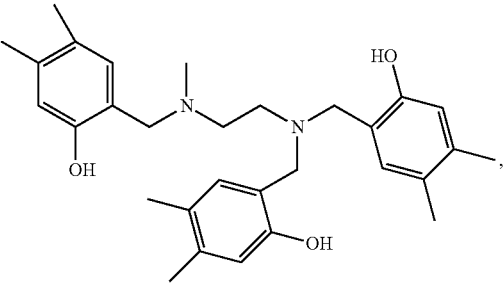
L17
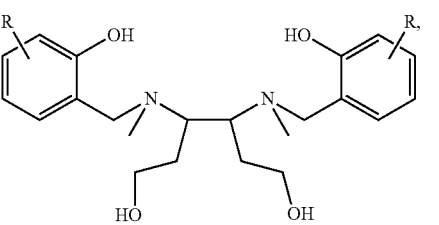
L18
wherein each R=H,

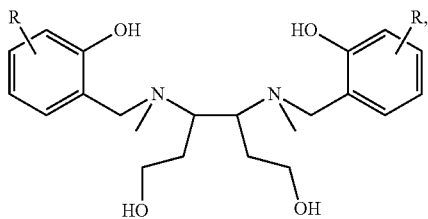

wherein each R=p-Me,

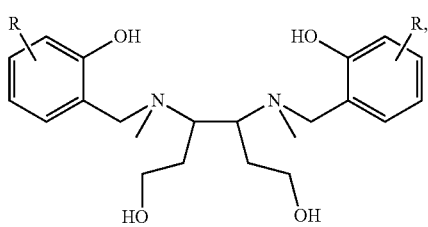

wherein each R=p-NO$_2$,

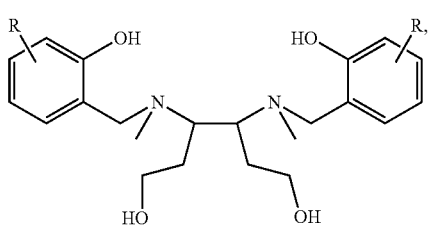

wherein each R=p-O-Me,

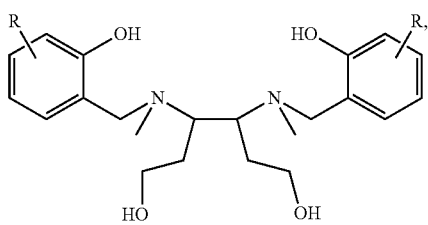

wherein each R=p-O-tBu,

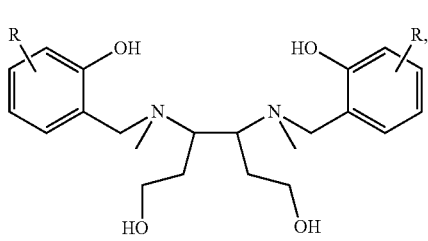

wherein each R=o,p-di-Me,

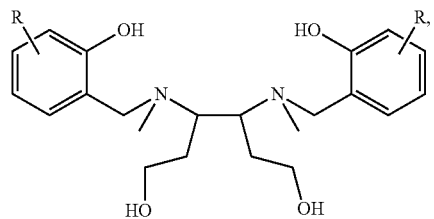

wherein each R=m,p-di-Me;

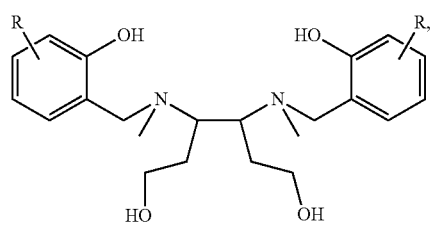

wherein each R represents a halide atom (Cl, Br, I or F), substituted para- to the hydroxyl groups,

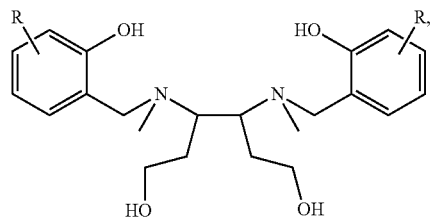

wherein each R represents two halide atoms (Cl, Br, I or F), substituted ortho- and para- to the hydroxyl groups,

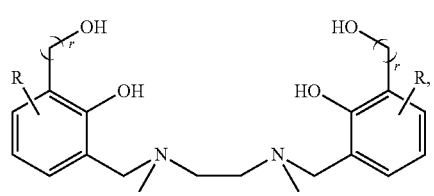

wherein each R=H, and r being an integer between 0 and 3,

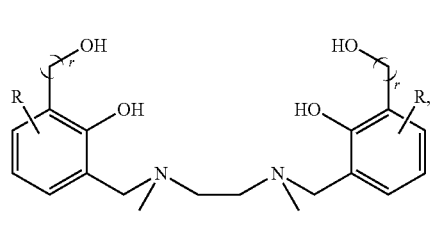

wherein each R=p-Me, and r being an integer between 0 and 3,

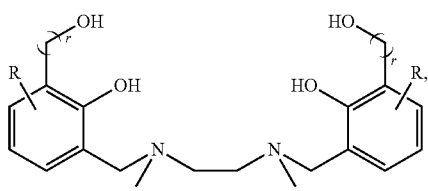

L29 wherein each R=p-NO$_2$, and r being an integer between 0 and 3,

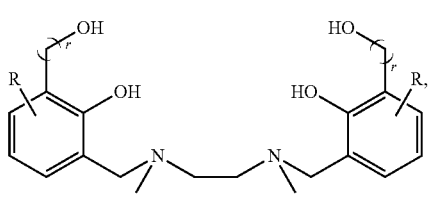

L30 wherein each R=p-O-Me, and r being an integer between 0 and 3,

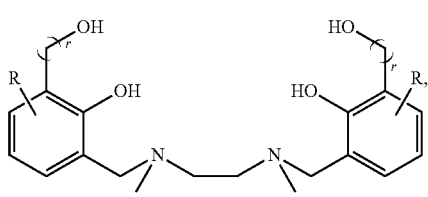

L31 wherein each R=p-O-tBu, and r being an integer between 0 and 3,

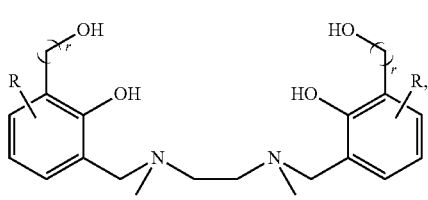

L32 wherein each R=o,p-di-Me, and r being an integer between 0 and 3;

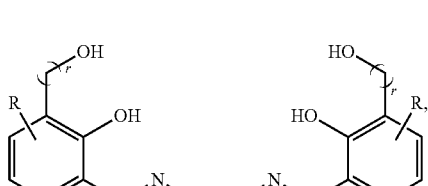

L33 wherein each R=m,p-di-, and r being an integer between 0 and 3,

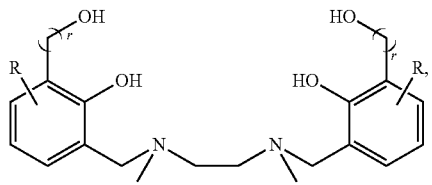

L34 wherein each R represents a halide atom (Cl, Br, I or F), substituted para- to the hydroxyl groups, and r being an integer between 0 and 3,

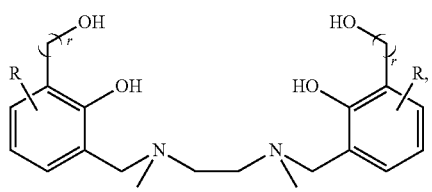

L35 wherein each R represents two halide atoms (Cl, Br, I or F), substituted ortho- and para- to the hydroxyl groups, and r being an integer between 0 and 3,

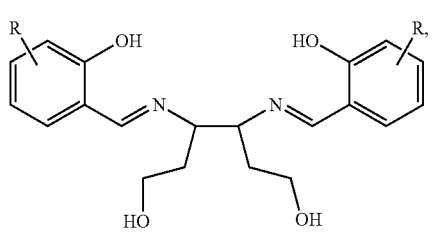

L36 wherein each R=H,

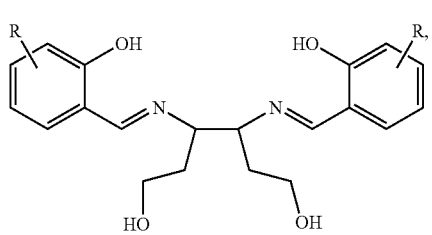

L37 wherein each R=p-Me,

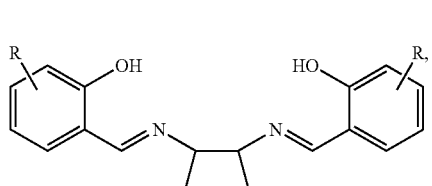

L38 wherein each R=p-NO$_2$,

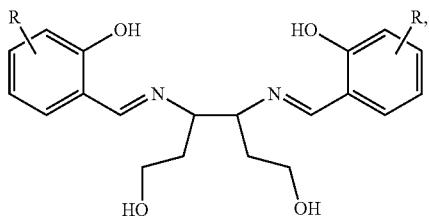
wherein each R=p-O-Me,
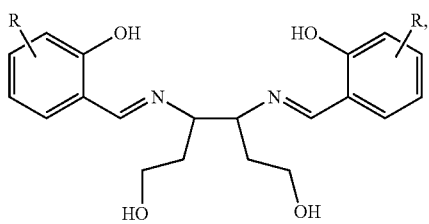
wherein each R=p-O-tBu,
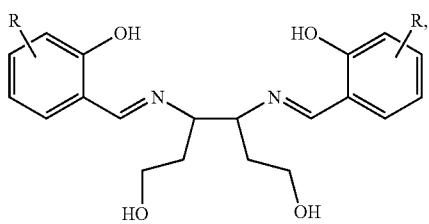
wherein each R=o,p-di-Me,
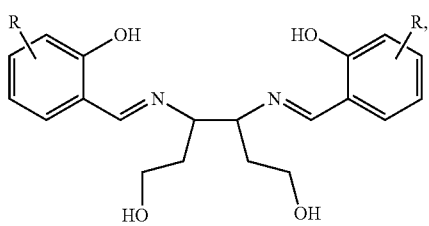
wherein each R=m,p-di-Me,
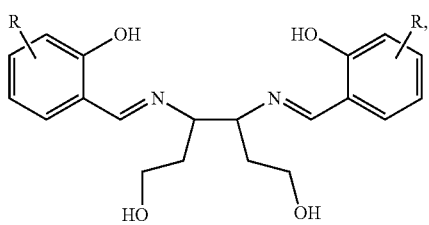
wherein each R represents a halide atom (Cl, Br, I or F), substituted para- to the hydroxyl groups,
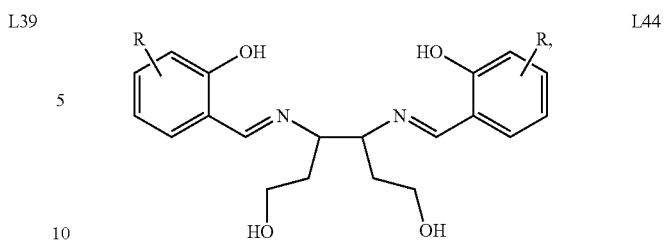
wherein each R represents two halide atoms (Cl, Br, I or F), substituted ortho- and para- to the hydroxyl groups,
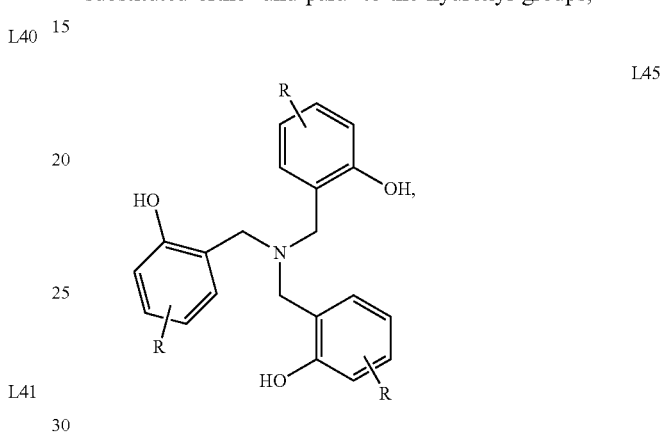
wherein each R=H,
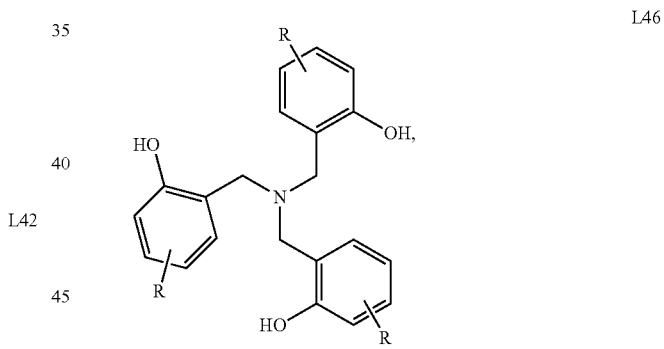
wherein each R=p-Me,
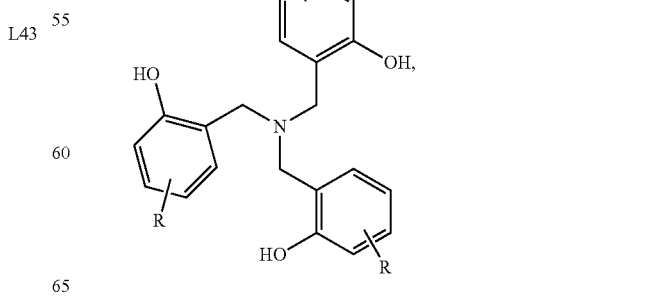
wherein each R=p-NO$_2$,

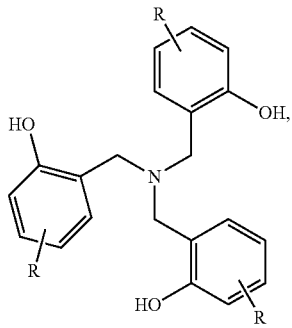
wherein each R=p-O-Me,
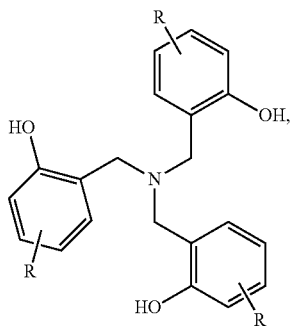
wherein each R=p-O-tBu,
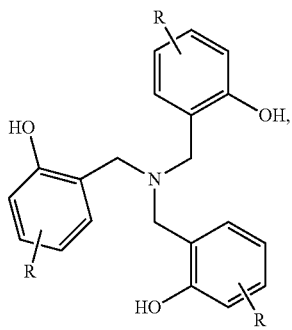
wherein each R=o,p-di-Me,
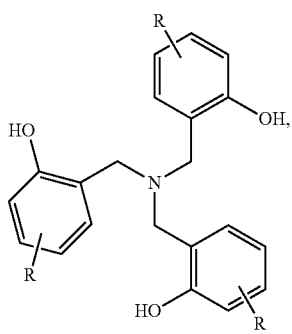
wherein each R=m,p-di-Me,
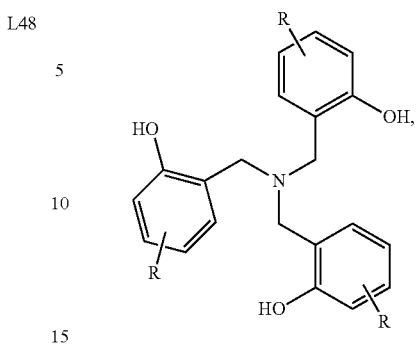
wherein each R represents a halide atom (Cl, Br, I or F), substituted para- to the hydroxyl groups,
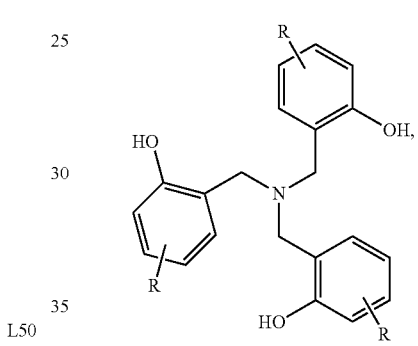
wherein each R represents two halide atoms (Cl, Br, I or F), substituted ortho- and para- to the hydroxyl groups,
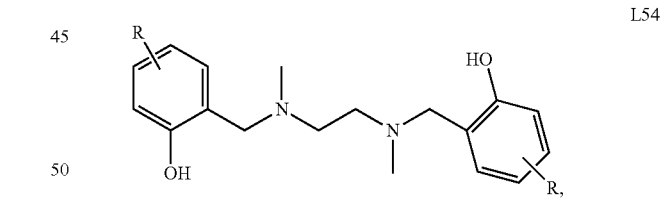
wherein each R=H,
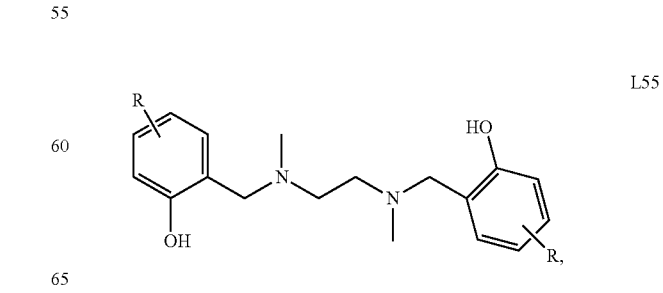
wherein each R=p-Me,

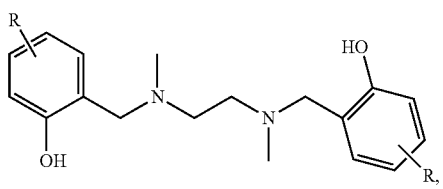

L56 wherein each R=p-NO$_2$,

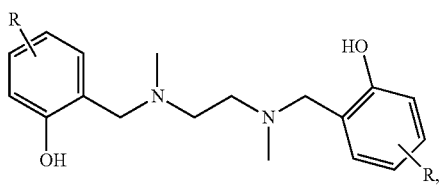

L57 wherein each R=p-O-Me,

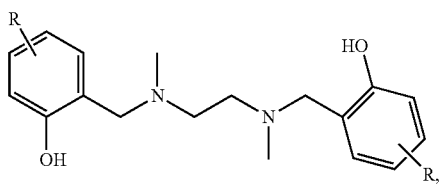

L58 wherein each R=p-O-tBu,

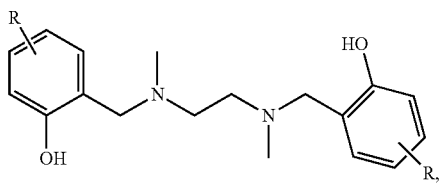

L59 wherein each R=o,p-di-Me,

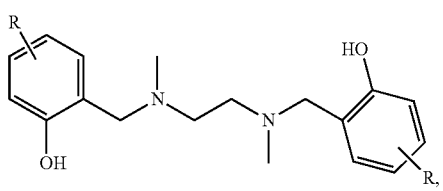

L60 wherein each R=m,p-di-Me,

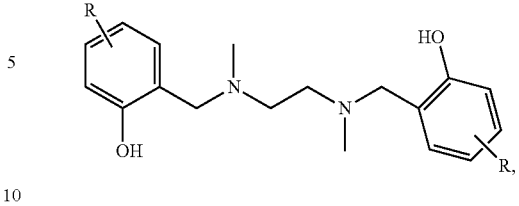

L61 wherein each R represents a halide atom (Cl, Br, I or F), substituted para- to the hydroxyl groups,

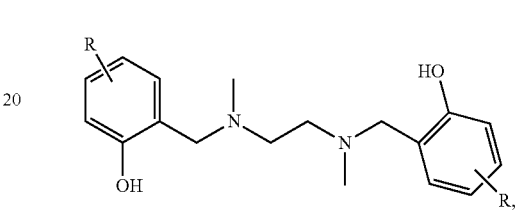

L62 wherein each R represents two halide atoms (Cl, Br, I or F), substituted ortho- and para- to the hydroxyl groups,

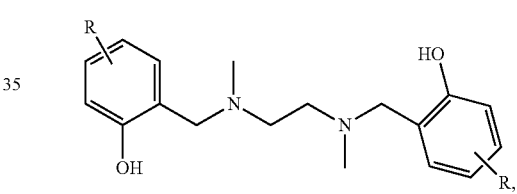

L63 wherein each R=H,

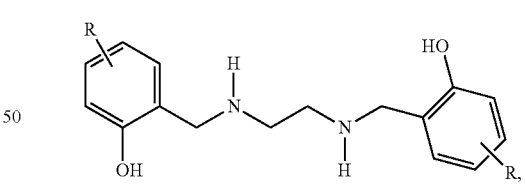

L64 wherein each R=p-Me,

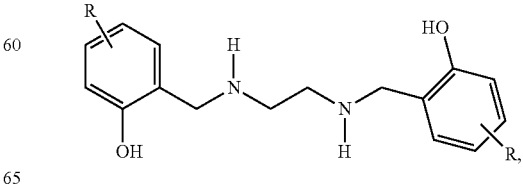

L65 wherein each R=p-NO$_2$,

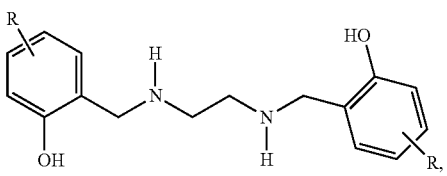

L66 wherein each R=p-O-Me,

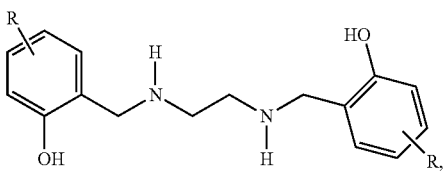

L67 wherein each R=p-O-tBu,

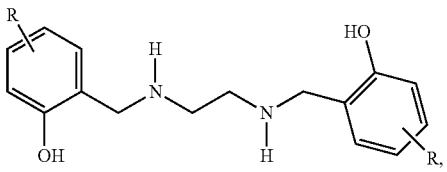

L68 wherein each R=o,p-di-Me,

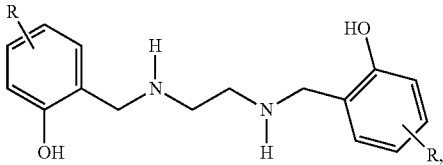

L69 wherein each R=m,p-di-Me,

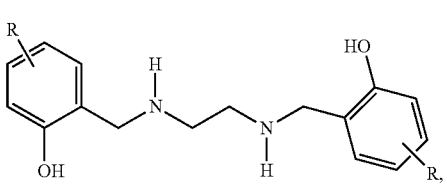

L70 wherein each R represents a halide atom (Cl, Br, I or F), substituted para- to the hydroxyl groups,

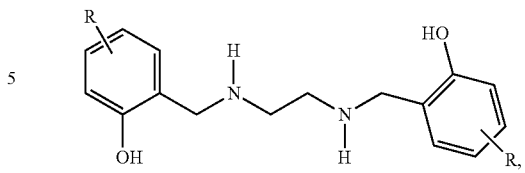

L71 wherein each R represents two halide atoms (Cl, Br, I or F), substituted ortho- and para- to the hydroxyl groups.

In some embodiments, the metal atom is titanium.

In other embodiments, the metal atom is vanadium or oxovanadium. In some embodiments, where the atom is oxovanadium, the ligand is not L63.

The metal M may be selected from titanium(IV), vanadium(V), oxovanadium(V), vanadium(IV) and oxovanadium(IV).

In some embodiments, the metal atom is titanium and the complex of the invention comprises a titanium (IV) atom covalently bound to a single polydentate ligand, with no labile groups, i.e., no monodentate groups. Thus, the invention relates to a Ti metal complex comprising a titanium atom covalently bound to a single polydentate ligand.

In other embodiments, the metal atom is vanadium and the complex of the invention comprises a vanadium (IV) or (V) atom covalently bound to a single polydentate ligand, with no labile groups, i.e., no monodentate groups. Thus, the invention relates to a V metal complex comprising a vanadium atom covalently bound to a single polydentate ligand and optionally to an oxo group (V=O), with the proviso that the metal complex is not compound 63.

In further embodiments, the ligand is bound to the metal (titanium or vanadium) atom via at least one heteroatom selected from nitrogen, oxygen and sulfur. In some embodiments, some of the bonds between the metal atom and the heteroatoms are covalent and some of the bonds are coordinative bonds.

In some embodiments, the covalent bonds to the metal atom are via oxygen or sulfur atoms. In some embodiments, the coordinative bonds to the metal atoms are via nitrogen or sulfur atoms.

In some embodiments, the metal atom is titanium atom being covalently bound to said ligand via four oxygen or sulfur atoms and coordinatively via two nitrogen or sulfur atoms.

In some embodiments, the ligand comprises at least one phenolato (ph-O—) group covalently bound to the metal atom via oxygen atom (ph-O—Ti—). In some embodiments, the metal atom is covalently bound to a single polydentate ligand comprising 1, 2, 3, or 4 phenolato groups. In such embodiments wherein the ligand comprises 1, 2, or 3 phenolato groups, the remaining groups may be alkoxy ($C_1$-$C_6$—O—) groups.

In some embodiments, the metal complex of the invention is of the general formula (I):

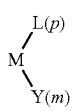

(I)

wherein

M being a metal atom selected from Ti, V and V=O;

L being a polydentate ligand associated via at least 3 covalent bonds to the metal atom, said ligand comprising at least one phenolato group; p being the number of phenolato groups in the polydentate ligand; p being 1, 2, 3 or 4;

Y may be absent or a labile monodentate ligand; m being the number of labile monodentate groups covalently bonded to the metal atom; m being zero (in which case the labile group is absent) or 1.

In some embodiments, m is 0.
In some embodiments, p is 1.
In some embodiments, p is 2.
In some embodiments, p is 3.
In some embodiments, p is 4.
In some embodiments, p is 1 and m is 0.
In some embodiments, p is 2 and m is 0.
In some embodiments, p is 3 and m is 0.
In some embodiments, p is 4 and m is 0.
In some embodiments, in the compound of formula (I) m=0, said compound being of the general formula (Ia):

M-L(p)    (Ia)

wherein M, L and p are as define hereinabove.
In some embodiments, p is 1.
In some embodiments, p is 2.
In some embodiments, p is 3.
In some embodiments, p is 4.

In some embodiments, in a compound of formula (Ia), ligand L is selected amongst ligands herein designated L1 through L70.

In some embodiments, in a compound according to formula (Ia), L is L1 or L2 or L3 or L4 or L5 or L6 or L7 or L8 or L9 or L10 or L11 or L12 or L13 or L14 or L15 or L16 or L17 or L18 or L19 or L20 or L21 or L22 or L23 or L24 or L25 or L26 or L27 or L28 or L29 or L30 or L31 or L32 or L33 or L34 or L35 or L36 or L37 or L38 or L39 or L40 or L41 or L42 or L43 or L44 or L45 or L46 or L47 or L48 or L49 or L50 or L51 or L52 or L53 or L54 or L55 or L56 or L57 or L58 or L59 or L60 or L61 or L62 or L63 or L64 or L65 or L66 or L67 or L68 or L69 or L70 or L71.

In some embodiments, L is selected from L1 or L2 or L3 or L4 or L5 or L6 or L7 or L8 or L9 or L10 or L11 or L12 or L13 or L14 or L15 or L17. In some embodiments, L is selected from L1, L2, L3, L4, L5, L6, L7, L8, L9, L10, L11, L12, L13, L14, L15 and L17.

Each of the polydentate ligands, e.g., L1-L71, may be oriented (associated) around the metal atom in a variety of fashions, depending, inter alia, on the selection of heteroatoms, the length of the linking groups bridging any two heteroatoms and the identity of the metal atom (M). Without wishing to be bound by theory or restricted by any one particular specific orientation provided below, the orientation may be any one of those depicted in Scheme 1 below:

Scheme 1

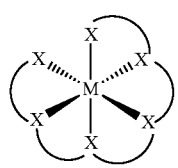
A

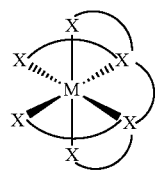
B

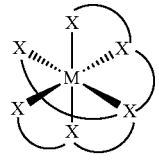
C

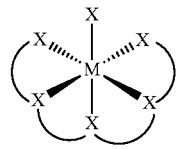
D

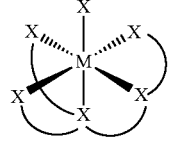
E

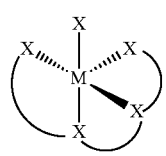
F

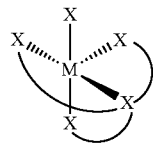
G

In the illustrated complexes of Scheme 1, each X represents a heteroatom selected from N, O and S. In some embodiments, X is selected independently from N and O. In some embodiments, the complex of the invention is of orientation B.

In some embodiments, the compound according to formula (I) is a compound of formula (II):

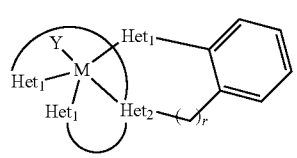
(II)

wherein
M is selected from Ti and V;
Y is selected from a labile monodentate group, an oxo group, a heteroatom and group of atoms comprising at least one heteroatom;
each of Het1 and Het2, independently of each other, is a heteroatom selected from N, O and S;
each curved line connecting Het1 and Het2, independently of the other, denoting a bond or linker moiety linking Het1 to Het2, and
r being zero or an integer between 1 and 3.

As used herein, the curved line

connecting any two atoms, particularly atoms designated Het1 or Het2, denotes a bond or a continuous chain of atoms (referred to also as a bridge or a linker moiety) linking the atoms at each of the two ends of the curved line. For example, in a compound of, e.g., formula (II) one of the atoms designated Het1 is linked to an atom designated Het2 with a curved line

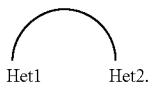

This means that Het1 is linked to Het2 via a bond (single, double or triple bond) or via a continuous chain of atoms (bridge or linker moiety) which may or may not contain one or more heteroatoms (selected from N, O and S). In a metal complex of e.g., formula (II), wherein each of Het1 and Het2 are directly bonded to the metal atom M (via covalent bond(s) or coordinative bond(s)), as in

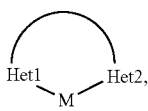

the curved line connecting Het1 and Het2, together with the metal atom M and atom Het1 and atom Het2 forms a ring structure, as defined.

The "ring structure" may be an aliphatic ring structure comprising a chain of carbon atoms (e.g., —$CH_2$—, —CH—, etc), wherein each carbon atom is sp3 hybridized; or may comprise one or more C—C double or triple bonds, which may or may not be endocyclic (wherein the double or triple bond is part of the continuous chain of atoms designated by the curved line). In some embodiments, the ring structure comprises a C═C bond which is endocyclic. The C═C bond may optionally be part of an aromatic ring, thus forming a fused ring structure of the general form A:

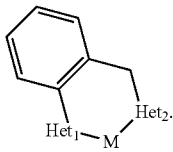

In some embodiments, as indicated hereinbelow, wherein Het1 is an oxygen atom, the ring structure depicted in A may be derived from a phenolato group.

In some embodiments, the ring structure formed between Het1 and Het2 (denoted by a curved line) comprises a single ring or a plurality of rings, the multiple ring system may be a fused ring system (such as the one exemplified by structure A above) or two or more bond-associated rings. The ring system (whether comprised of a single ring or a plurality of rings) may comprise one or more aliphatic bridges and/or one or more aromatic bridges (each bridge being denoted by a curved line), forming together with the Het1/Het2 and the metal atoms a corresponding ring structure; the bridges (whether aliphatic and/or aromatic) may be fused or bonded to a $C_3$-$C_6$ carbon chain comprising sp3 hybridized carbon atoms and optionally at least one C—C double or triple bonds; or may be bonded to at least one $C_6$-$C_{10}$ aromatic ring; or may be substituted by a $C_1$-$C_6$alkyl or $C_6$-$C_{10}$ aromatic group.

In some embodiments, at least one bond of the multiple ring system being a covalent or coordinative bond to the metal atom.

In some embodiments, the compound of formula (II) is a compound wherein M is V atom and Y is ═O (together with the V atom forming an oxovanadium, V═O).

In some embodiments, the compound of formula (II) is a compound wherein M is Ti atom and Y is absent or is a labile monodentate group.

In some embodiments, each of the aryl (aromatic) rings depicted in the structure of formula (II) or any formulae according to the invention, unless otherwise stated, may be substituted by at least one atom or group of atoms selected from —H, halide (Cl, F, I and Br), —$C_1$-$C_6$alkyl, —$C_2$-$C_6$alkenyl, —$C_2$-$C_6$alkynyl, —$C_6$-$C_{10}$aryl, —OH, —$OC_1$-$C_6$alkyl, —$NR_5R_6$ and —$NO_2$.

In some embodiments, the compound of formula (II) is a compound of formula (IIa):

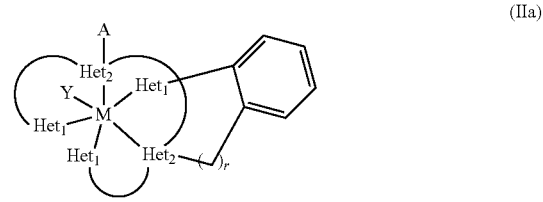

(IIa)

wherein

M is selected from Ti and V;

Y is selected from a labile monodentate group, an oxo group, a heteroatom and a group of atoms comprising at least one heteroatom;

each of Het1 and Het2, independently of each other, is a heteroatom selected from N, O and S;

each curved line connecting Het1 and Het2 or Het2 and a further Het2, independently of the other, denoting a bond or linker moiety linking the atoms, as defined above, r being zero or an integer between 1 and 3, and A is selected from —H, a —$C_1$-$C_6$alkyl, —$C_3$-$C_6$alkenyl and —$C_3$-$C_6$alkynyl.

In some embodiments, at least one of the linker moieties between Het1 and Het2 or Het2 and a further Het2 (denoted by a curved line between the atoms) is an aliphatic bridge selected from —$C_1$-$C_6$alkylene, —$C_2$-$C_6$alkenylene and —$C_2$-$C_6$alkynylene.

In some embodiments, at least one of the linker moieties between Het1 and Het2 or Het2 and a further Het2 (denoted by a curved line) is an aliphatic bridge selected from —$C_1$-$C_6$alkylene. In some embodiments, said —$C_1$-$C_6$alkylene is selected from methylene, ethylene, propylene, butylenes and pentylene. In some embodiments, said —$C_1$-$C_6$alkylene is ethylene.

In some embodiments, the linking moiety linking Het2 and a further Het2 is a —C$_1$-C$_6$alkylene, being optionally ethylene.

In some embodiments, the compound of formula (IIa) is a compound of formula (IIb):

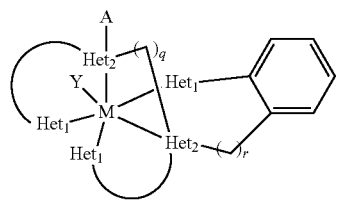

(IIb)

wherein

M is selected from Ti and V;

Y is selected from a labile monodentate group, an oxo group, a heteroatom and a group of atoms comprising at least one heteroatom;

each of Het$_1$ and Het$_2$, independently of each other, is a heteroatom selected from N, O and S;

each curved line connecting Het1 and Het2, independently of the other, denoting a bond or linker moiety linking Het1 to Het2, as defined above, r being zero or an integer between 1 and 3, q being an integer between 1 and 4, and A is selected from —H, a —C$_1$-C$_6$alkyl, —C$_3$-C$_6$alkenyl and —C$_3$-C$_6$alkynyl.

In some embodiments, r is 1 and q is 2.

In some embodiments, Y is a labile group. Wherein Y is a labile group, it is susceptible to hydrolysis under physiological conditions. In such embodiments, Y may be selected from halide (halo), amine, mono- or di- or tri-substituted amine (wherein substitution of the N atom is by one, two or three different or same —C$_1$-C$_6$alkyl group, —C$_1$-C$_6$ alkyl, —SH, —SC$_1$-C$_6$alkyl, —OH and —OC$_1$-C$_6$alkyl.

In some embodiments, wherein the labile group is a quaternary amine, the N atom is protonated or alkylated to a charged state, forming a salt with, e.g., at least one pharmaceutically acceptable counter-ion.

Wherein Y is a labile group, it may be of any number of atoms, which may or may not comprise a heteroatom (e.g., N, O, S). The labile group is typically selected to be susceptible to hydrolysis, e.g., under physiological conditions (or environment), and thus may be selected from monodentate ligands. The labile group is said of being a "monodentate" group; in other words, the labile group (Y) forms a single bond with the metal atom.

According to some embodiments of the invention, Y is halide; said halide being optionally —Cl.

In some embodiments, Y is selected from a charged heteroatom selected from O$^-$, S$^-$ or N$^+$.

According to other embodiments, Y is selected from —C$_1$-C$_6$alkyl, —OC$_1$-C$_6$alkyl and —SC$_1$-C$_6$alkyl. In some embodiments, Y is a —OC$_1$-C$_6$alkyl. In some embodiments, the alkyl in said —OC$_1$-C$_6$alkyl may be iso-propyl (iPr).

In some embodiments, the compound of formula (II) is a compound of formula (IIc):

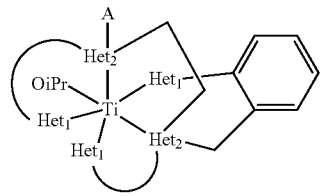

(IIc)

wherein each of A, Het1 and Het2 is as defined above.

In some embodiments, in a compound of formula (IIc), each of said linker moieties (denoted by curved lines) being a phenolato structure, said phenolato being optionally substituted.

In some embodiments, in a compound of formula (IIc) each of said ring structure being an aliphatic ring structure, being optionally substituted.

In some embodiments, in a compound of any one of formulae (II), (IIa), (IIb) and (IIc), Het1 is selected from O and S.

In some embodiments, in a compound of any one of formulae (II), (IIa), (IIb) and (IIc), Het2 is selected from N and S.

In some embodiments, in a compound of any one of formulae (II), (IIa), (IIb) and (IIc), Het1 is selected to form a covalent bond to M and Het2 is selected to form a coordinative bond to M.

In some embodiments, in a compound of formula (IIc), each of said linker moieties is a phenolato structure being optionally substituted, the compound being a compound of formula (IId):

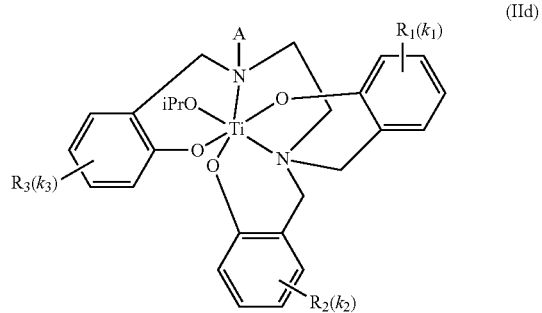

(IId)

wherein

A is selected from a —C$_1$-C$_6$alkyl, —C$_3$-C$_6$alkenyl and —C$_3$-C$_6$alkynyl; each of R$_1$, R$_2$ and R$_3$, independently of the other, is selected from halide, —C$_1$-C$_6$alkyl, —C$_2$-C$_6$alkenyl, —C$_2$-C$_6$alkynyl, —C$_6$-C$_{10}$aryl, —OH, —OC$_1$-C$_6$alkyl, —NR$_5$R$_6$ and —NO$_2$;

each of k$_1$, k$_2$, and k$_3$ being an integer denoting the number of substitutions (of groups R$_1$, R$_2$, or R$_3$) on each ring; each of k$_1$, k$_2$, and k$_3$, independently of the other, being selected from 1, 2, 3 and 4;

in cases where at least one of R$_1$, R$_2$ and R$_3$ is —NR$_5$R$_6$, each of R$_5$ and R$_6$, independently of the other, is selected from —H and —C$_1$-C$_6$alkyl.

In some embodiments, at least one of R$_1$, R$_2$, and R$_3$ is —H.

In some embodiments, at least one of R$_1$, R$_2$, and R$_3$ is halide (Cl, Br, F or I).

In some embodiments, at least one of $R_1$, $R_2$, and $R_3$ is —$C_1$-$C_6$alkyl.

In some embodiments, each of $R_1$, $R_2$, and $R_3$ is —$C_1$-$C_6$alkyl.

In some embodiments, each of $R_1$, $R_2$, and $R_3$ is halide (Cl, Br, F or I).

In some embodiments, each of the phenolato ring structures being substituted by 1 or 2 substituents, each of said substituents being selected from halide (Cl, Br, F or I), —$C_1$-$C_6$alkyl, —$C_2$-$C_6$alkenyl, —$C_2$-$C_6$alkynyl, —$C_6$-$C_{10}$aryl, —OH, —$OC_1$-$C_6$alkyl, —$NR_5R_6$ and —$NO_2$, as defined herein.

In some embodiments, each phenolato being substituted by 2 substituents selected from halide (Cl, Br, F or I) and —$C_1$-$C_6$alkyl. In some embodiments, the two substituents are positioned para-, meta- or ortho- to each other. Each pair of substituents may or may not be identical to a second or further pair of substituents on a different phenolato ring.

In some embodiments, one of the substituents is positioned at a vicinal (ortho-) position to the phenolato bond (i.e., bond connecting the benzene ring to the oxygen atom of the phenolato ring system). In other embodiments, at least one of the substituents is positioned meta- to the phenolato bond.

In some embodiments, wherein each phenolato ring is substituted by two substituents, said substituents may be positioned at positions 1,2 or 1,3 or 1,4 or 2,3 or 2,4 with respect to the oxygen atom (where "position 1" to the O atom is the carbon atom ortho to the ipso-carbon).

In some embodiments, the two substituents are positioned meta- or ortho- to each other.

In some embodiments, the compound of formula (IId) is a compound of formulae (IIe) or (IIf):

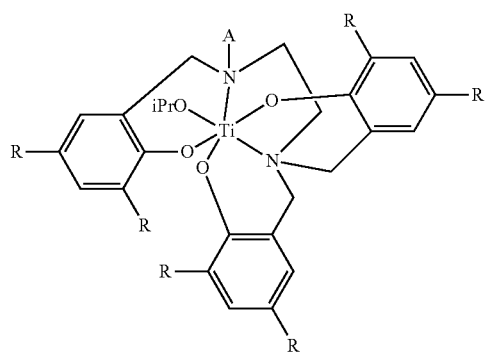

(IIe)

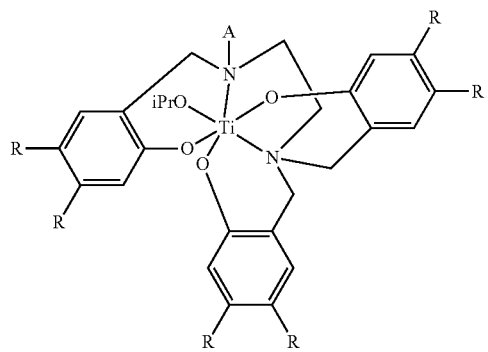

(IIf)

wherein in a compound of formula (IIe) or formula (IIf), each A is selected as above and each of R, independently of the other R's in the same or other formula, is selected from halide (Cl, Br, F or I), —$C_1$-$C_6$alkyl, —$C_2$-$C_6$alkenyl, —$C_2$-$C_6$alkynyl, —$C_6$-$C_{10}$aryl, —OH, —$OC_1$-$C_6$alkyl, —$NR_5R_6$ and —$NO_2$.

In some embodiments, each R is selected independently from halide (Cl, Br, F or I) and —$C_1$-$C_6$alkyl.

It should be noted that in cases where the depicted substitutions are of a substituent designated by the letter R, as is the case in the compounds of formulae (IIe) and MO, each R may be the same or different. The identical designation by the letter R of ring substitutions does not necessarily indicate substitutions by only 1, only 2, only 3 or 4 substitutions, nor does it necessarily indicate substitution by the same groups or atoms. In other words, each substitution is independently selected.

In some embodiments, in a single compound of a general formula of the invention, all ring substitutions designated by the letter R are the same. In other embodiments, each substitution is independently different.

In some embodiments, each of R is a halide. In some embodiments, said halide is —Cl.

In some embodiments, each of R is —$C_1$-$C_6$alkyl. In some embodiments, said —$C_1$-$C_6$alkyl is a methyl.

In some embodiments, in a compound of formulae (II), (IIa) and (IIb), Y is not a labile group.

In some embodiments, in a compound of formula (II), (IIa) and (IIb), Y is a heteroatom selected from N, O and S, or a group of atoms comprising at least one heteroatom, said heteroatom forming a bond with a carbon atom in A, the compound having the formula (IIg):

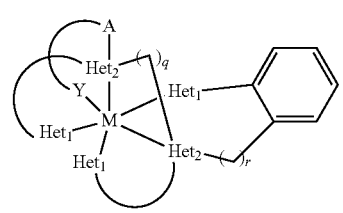

(IIg)

wherein each of M, A, Y, Het1 and Het2, q and r is as defined above.

In some embodiments, q is 2, r is 1 and M is Ti.

In some embodiments, the compound of formula (II) is a compound of formula (III):

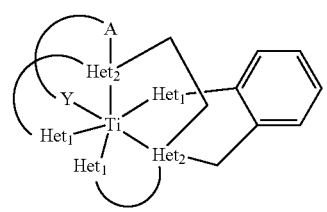

(III)

wherein
Y, A, Het1 and Het2 are as defined above, and wherein each curved line connecting Het1 to Het2 and Y to A constitutes a linker moiety.

In some embodiments, each of said Het1 is an oxygen atom.

In some embodiments, each of said Het2 is a nitrogen atom.

In some embodiments, Y is an oxygen atom and A is a carbon atom (e.g., in a group of atoms), said Y and A forming together a ring structure.

In some embodiments, in a compound of formulae (II) or (III), each of said ring structures being or containing a phenolato structure, said phenolato being optionally substituted.

In some embodiments, in a compound of formulae (II) or (III) each of said ring structures being or containing an aliphatic ring structure, being optionally substituted.

In some embodiments, in a compound of formula (III), each of said ring structures is a phenolato structure being optionally substituted, the compound being a compound of formula (IV):

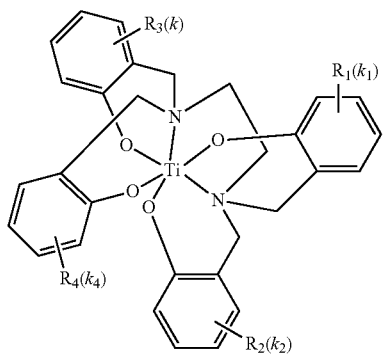

(IV)

wherein
each of $R_1$, $R_2$, $R_3$ and $R_4$, independently of the other, is selected from halide (Cl, Br, F or I), —$C_1$-$C_6$alkyl, —$C_2$-$C_6$alkenyl, —$C_2$-$C_6$alkynyl, —$C_6$-$C_{10}$aryl, —OH, —$OC_1$-$C_6$alkyl, —$NR_5R_6$ and —$NO_2$;

each of k, $k_1$, $k_2$, and $k_3$ being an integer designating the number of substitutions (of groups $R_1$, $R_2$, $R_3$ or $R_4$) on each ring; each of k, $k_1$, $k_2$, and $k_3$, independently of the other, being selected from 1, 2, 3 and 4;

each of $R_5$ and $R_6$, independently of the other, being selected from —H and —$C_1$-$C_6$alkyl.

In some embodiments, at least one of $R_1$, $R_2$, $R_3$ and $R_4$ is —H.

In some embodiments, at least one of $R_1$, $R_2$, $R_3$ and $R_4$ is halide (Cl, Br, F or I).

In some embodiments, at least one of $R_1$, $R_2$, $R_3$ and $R_4$ is —$C_1$-$C_6$alkyl.

In some embodiments, each of $R_1$, $R_2$, $R_3$ and $R_4$ is —$C_1$-$C_6$alkyl.

In some embodiments, each of $R_1$, $R_2$, $R_3$ and $R_4$ is halide (Cl, Br, F or I).

In some embodiments, each of the phenolato ring structures being substituted by 1 or 2 substituents, each of said substituents being selected from halide (Cl, Br, F or I), —$C_1$-$C_6$alkyl, —$C_2$-$C_6$alkenyl, —$C_2$-$C_6$alkynyl, —$C_6$-$C_{10}$aryl, —OH, —$OC_1$-$C_6$alkyl, —$NR_5R_6$ and —$NO_2$.

In some embodiments, each phenolato being substituted by 2 substituents selected from halide (Cl, Br, F or I) and —$C_1$-$C_6$alkyl. In some embodiments, the two substituents are positioned para-, meta- or ortho- to each other. Each pair of substituents may or may not be identical to a second or further pair of substituents on a different phenolato ring.

In some embodiments, one of the substituents is positioned at a vicinal (ortho-) position to the phenolato bond (i.e., bond connecting the benzene ring to the oxygen atom of the phenolato ring system). In other embodiments, at least one of the substituents is positioned meta- to the phenolato bond.

In some embodiments, wherein each phenolato ring is substituted by two substituents, said substituents may be positioned at positions 1,2 or 1,3 or 1,4 or 2,3 or 2,4 with respect to the oxygen atom (where "position 1" to the O atom is the carbon atom ortho to the ipso-carbon).

In some embodiments, the two substituents are positioned meta- or ortho- to each other.

In some embodiments, the compound of formula (IV) is a compound of formula (IVa):

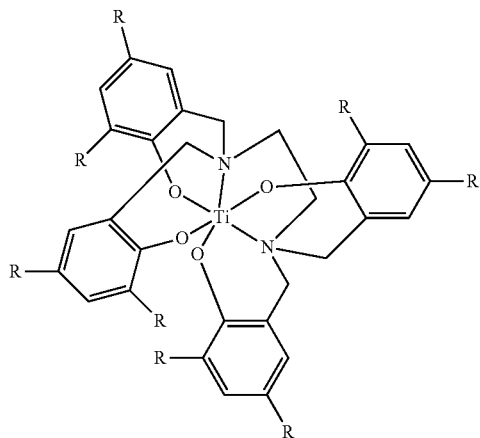

(IVa)

wherein
each R being selected independently from halide (Cl, Br, F or I) and —$C_1$-$C_6$alkyl.

In some embodiments, each of R is a halide. In some embodiments, said halide is —Cl.

In some embodiments, each of R is —$C_1$-$C_6$alkyl. In some embodiments, said —$C_1$-$C_6$alkyl is a methyl.

In some embodiments, the compound of formula (IV) is a compound of formula (IVb):

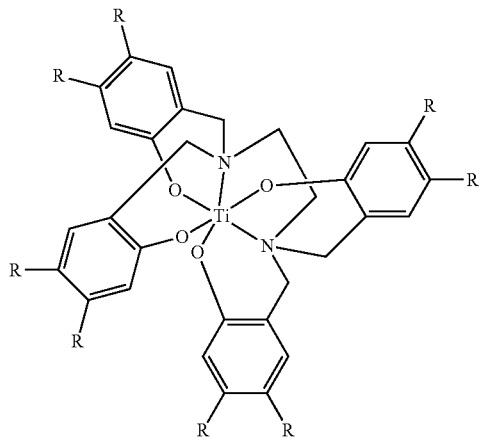

(IVb)

wherein
each of R being selected independently from halide (Cl, Br, F or I) and —$C_1$-$C_6$alkyl.

In some embodiments, each of the groups designated by the letter R is a halide. In some embodiments, said halide is —Cl.

In some embodiments, each of the groups designated by the letter R is —$C_1$-$C_6$alkyl. In some embodiments, said —$C_1$-$C_6$alkyl is a methyl.

In some embodiments, the compound of the invention is selected from:

Compound 1

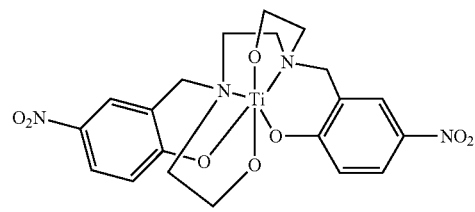

Compound 2

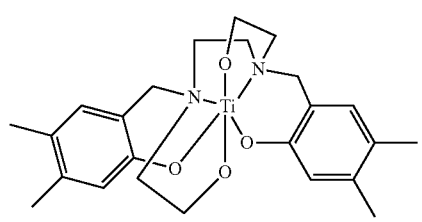

Compound 3

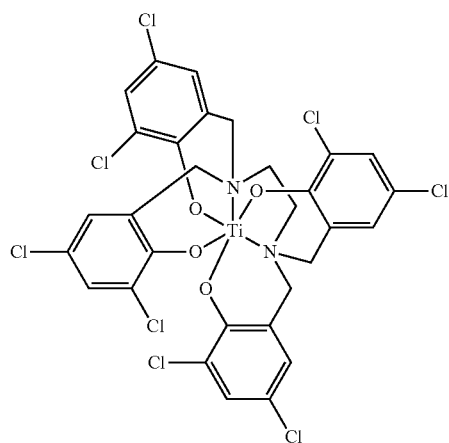

Compound 4

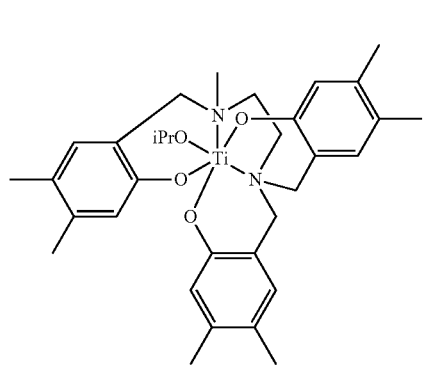

Compound 5

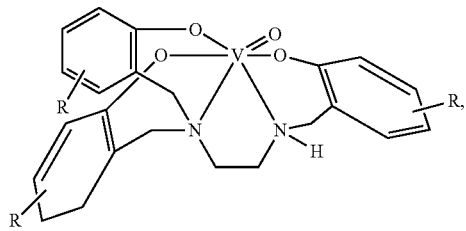

wherein each R=H

Compound 6

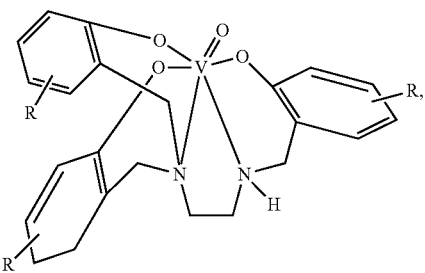

wherein each R=p-Me

Compound 7

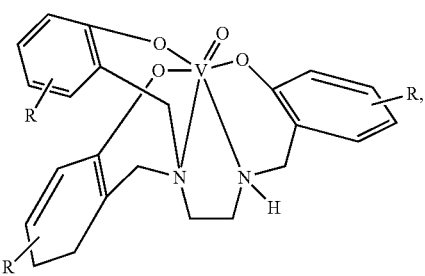

wherein each R=p-Cl

Compound 8

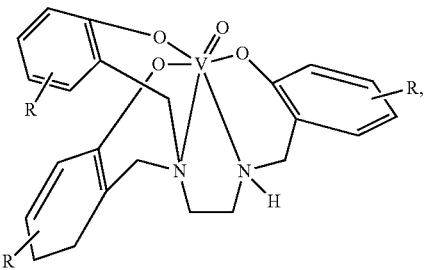

wherein each R=p-O-Me

Compound 9
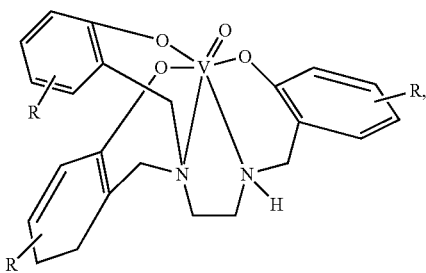
wherein each R=p-O-tBu
Compound 45
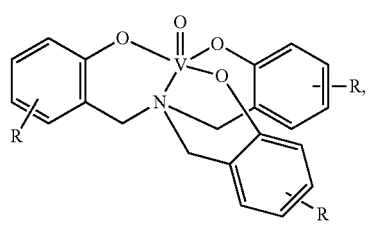
wherein each R=H
Compound 46
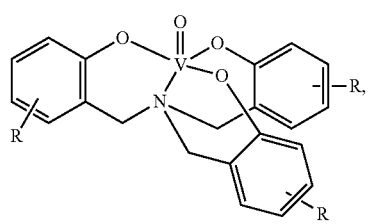
wherein each R=p-Me
Compound 47
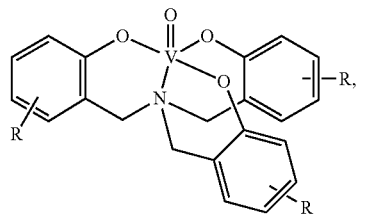
wherein each R=p-Cl
Compound 48
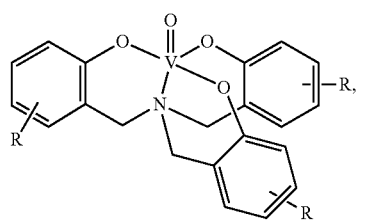
wherein each R=p-O-Me
Compound 49
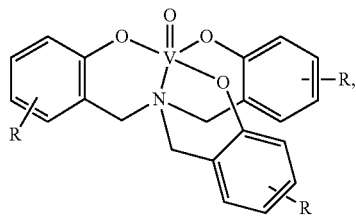
wherein each R=p-O-tBu
Compound 50
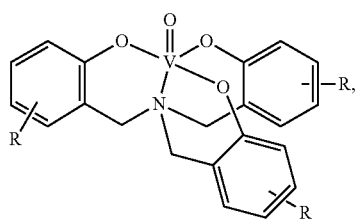
wherein each R=o,p-di-Me represents two methyl groups at positions 2 and 4;
Compound 54
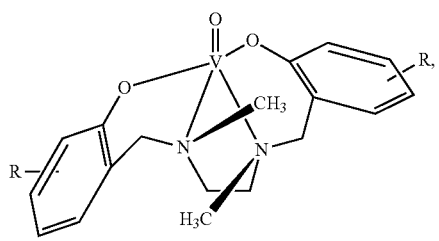
wherein each R=H
Compound 55
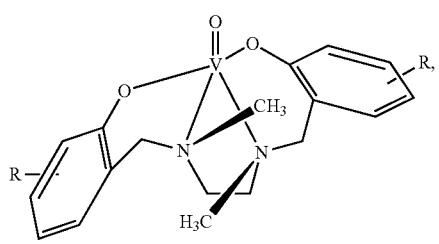
wherein each R=p-Me
Compound 56
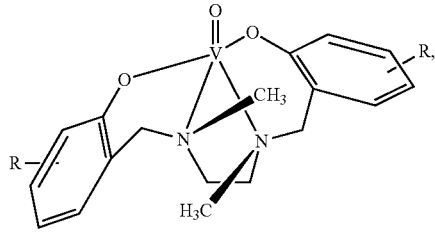
wherein each R=p-NO$_2$ Compound 57

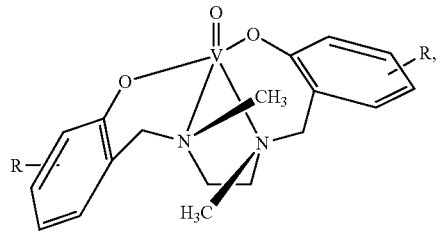

wherein each R=p-O-Me

Compound 58

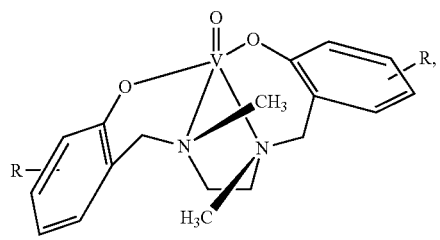

wherein each R=p-O-tBu

Compound 64

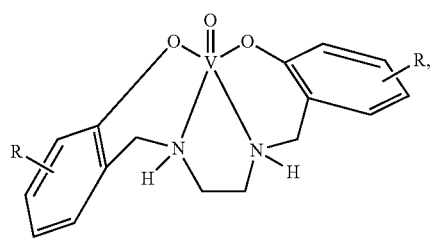

wherein each R=p-Me

Compound 65

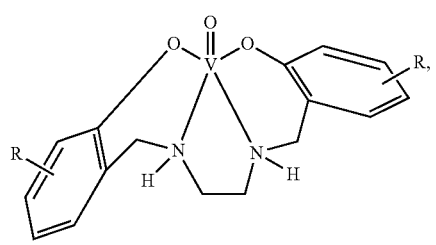

wherein each R=p-NO$_2$

Compound 66

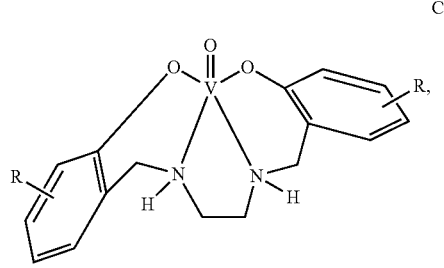

wherein each R=p-O-Me

Compound 67

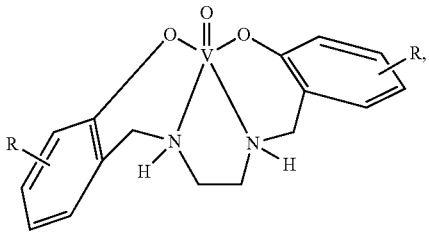

wherein each R=p-O-tBu

In other embodiments, the metal complexes of the invention are any one or more of those listed in Table 1 below.

TABLE 1 metal complexes according to the present invention

| Compound No. | Metal | Ligand |
|---|---|---|
| 1 | Ti | L6 |
| 2 | Ti | L5 |
| 3 | Ti | L15 (R = o, p-Cl) |
| 4 | Ti | L17 |
| 5 | V=O | L7 |
| 6 | V=O | L8 |
| 7 | V=O | L9 |
| 8 | V=O | L10 |
| 9 | V=O | L11 |
| 10 | Ti | L12 |
| 11 | Ti | L13 |
| 12 | Ti | L14 |
| 13 | Ti | L16 |
| 14 | Ti | L1 |
| 15 | Ti | L2 |
| 16 | Ti | L3 |
| 17 | Ti | L4 |
| 18 | Ti | L18 |
| 19 | Ti | L19 |
| 20 | Ti | L20 |
| 21 | Ti | L21 |
| 22 | Ti | L22 |
| 23 | Ti | L23 |
| 24 | Ti | L24 |
| 25 | Ti | L25 |
| 26 | Ti | L26 |
| 27 | Ti | L27 |
| 28 | Ti | L28 |
| 29 | Ti | L29 |
| 30 | Ti | L30 |
| 31 | Ti | L31 |
| 32 | Ti | L32 |
| 33 | Ti | L33 |
| 34 | Ti | L34 |
| 35 | Ti | L35 |
| 36 | Ti | L36 |
| 37 | Ti | L37 |
| 38 | Ti | L38 |
| 39 | Ti | L39 |
| 40 | Ti | L40 |
| 41 | Ti | L41 |
| 42 | Ti | L42 |
| 43 | Ti | L43 |
| 44 | Ti | L44 |
| 45 | V=O | L45 |
| 46 | V=O | L46 |
| 47 | V=O | L47 |
| 48 | V=O | L48 |
| 49 | V=O | L49 |
| 50 | V=O | L50 |
| 51 | V=O | L51 |
| 52 | V=O | L52 |
| 53 | V=O | L53 |
| 54 | V=O | L54 |
| 55 | V=O | L55 |

TABLE 1-continued metal complexes according to the present invention

| Compound No. | Metal | Ligand |
|---|---|---|
| 56 | V=O | L56 |
| 57 | V=O | L57 |
| 58 | V=O | L58 |
| 59 | V=O | L59 |
| 60 | V=O | L60 |
| 61 | V=O | L61 |
| 62 | V=O | L62 |
| 63 | V=O | L63 |
| 64 | V=O | L64 |
| 65 | V=O | L65 |
| 66 | V=O | L66 |
| 67 | V=O | L67 |
| 68 | V=O | L68 |
| 69 | V=O | L69 |
| 70 | V=O | L70 |
| 71 | V=O | L71 |

In some embodiments, the compound of the invention is Compound 1 or Compound 2 or Compound 3 or Compound 4 or Compound 5 or Compound 6 or Compound 7 or Compound 8 or Compound 9 or Compound 45 or Compound 46 or Compound 47 or Compound 48 or Compound 49 or Compound 50 or Compound 54 or Compound 55 or Compound 56 or Compound 57 or Compound 58 or Compound 64 or Compound 65 or Compound 66 or Compound 67 or Compound 68 or Compound 69.

As used herein, the "phenolato" group refers to a phenol ring structure (—O-Ph, wherein Ph represents a phenyl ring), wherein the oxygen atom is covalently bonded to the metal atom and the phenyl ring being further substituted to form a further (second) association with the metal atom. The association may be directly (wherein integer r is 0), via a methylene (wherein integer r is 1) or via a longer linking moiety (wherein the integer r is between 2 or 3). The phenyl ring may be further substituted as defined herein.

As used herein, the term "—$C_1$-$C_6$alkyl" refers to a straight or branched aliphatic chain containing between 1 and 6 carbon atoms, which may or may not be substituted. Non-limiting examples of such alkyl chains include methyl, ethyl, propyl, iso-propyl, iso-butyl, n-butyl, sec-butyl, tert-butyl, pentyl, and iso-hexyl. The term "—$C_1$-$C_6$alkylene" refers to a straight, branched or cyclic, in certain embodiments straight or branched, divalent aliphatic hydrocarbon group, having from 1 to 6 carbon atoms. Non-limiting examples of alkylenes include methylene (—$CH_2$—), ethylene (—$CH_2CH_2$—), propylene, iso-propylene, iso-butylene, n-butylene, sec-butylene, tert-butylene, pentylene, and iso-hexylene.

As used herein, "—$C_2$-$C_6$alkenylene" refers to a straight, branched or cyclic divalent aliphatic hydrocarbon group, having from 2 to 6 carbon atoms and at least one double bond. Alkenylene groups include, but are not limited to, —CH=CH—CH=CH— and —H=CH—$CH_2$—.

As used herein, "—$C_2$-$C_6$alkynylene" refers to a straight, branched or cyclic divalent aliphatic hydrocarbon group, having from 2 to 6 carbon atoms and at least one triple bond. Alkynylene groups include, but are not limited to, —C≡C—C≡C—, —C≡C— and —C≡C—$CH_2$—.

The term "—$OC_1$-$C_6$alkyl" refers, in the context of the present invention, to an oxygen atom substituted at one end to the skeleton of formula (I) and at the other end to a —$C_1$-$C_6$alkyl, as defined above. Similarly, "—$SC_1$-$C_6$alkyl" refers to a sulfur atom substituted at one end to the skeleton of formula (I) and at the other end to a —$C_1$-$C_6$alkyl, as defined above.

The term "halide" used interchangeably with "halo" refers to a compound selected from fluoro (F), chloro (Cl), bromo (Br), and iodo (I). In some embodiments, the halide is chloro (Cl).

As used herein, "—$C_6$-$C_{10}$aryl" refers, in the context of the present invention, to an aromatic ring system having between 6 and 10 carbon atoms. The term "—$C_1$-$C_6$alkylenearyl" refers to an aryl substituted by a —($C_1$-$C_6$) alkyl group. In some embodiments, the aryl is a substituted or unsubstituted phenyl or a substituted or unsubstituted naphthyl group.

The aryl group may alternatively be a "heteroaryl" group comprising at least 4 carbon atoms and one or more additional heteroatom selected from N, O and S. The heteroaryl refers to a monocyclic or multicyclic aromatic ring system, in certain embodiments, of about 5 to about 15 atoms, where one or more, the atoms in the ring system is a heteroatom. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, "—$OC_6$-$C_{10}$aryl" refers, in the context of the present invention, to an oxygen atom substituted at one end to the skeleton of formula (I) and at the other end to a —($C_6$-$C_{10}$)aryl, as defined above.

The term "—$NR_5R_6$" refers to an amine group selected from a primary amine (wherein each of $R_5$ and $R_6$ is —H), a secondary amine (wherein one of $R_5$ and $R_6$ is a —$C_1$-$C_6$alkyl) or a tertiary amine (wherein each of $R_5$ and $R_6$ is a —$C_1$-$C_6$alkyl, $R_5$ and $R_6$ need not be the same). In some embodiments, the —$NR_5R_6$ may represent a quaternary amine, wherein the N atom is further protonated or alkylated to a charged state, forming a salt with, e.g., at least one pharmaceutically acceptable counter-ion.

In some embodiments, $R_5$ and $R_6$ in —$NR_5R_6$ form a cyclic structure with the N atom they are bonded to; the cyclic amine having between 3 and 6 atoms in the hetero-ring structure. In some embodiments, the hetero-ring comprises, apart from the N atom, one or more additional heteroatoms selected from N, O and S. In further embodiments, the hetero-ring comprises a single heteroatom (the N atom of the —$NR_5R_6$ group) with the remaining atoms being carbon atoms.

It is another aspect of the present invention to provide a composition comprising a compound of formula (I) or (Ia) or (II) or (IIa) or (IIb) or (IIc) or (IId) or (IIe) or (IIf) or (IIg) or (III) or (IV) or (IVa) or (IVb), as defined hereinabove. In some embodiments, said compound is at least one compound of formula (I), wherein the metal is Ti and the ligand L is selected amongst ligands designated L1 through L71.

In some embodiments, the compound is selected from compounds herein designated Compound 1, Compound 2, Compound 3, Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, Compound 23, Compound 24, Compound 25, Compound 26, Compound 27, Compound 28, Compound 29, Compound 30, Compound 31, Compound 32, Compound 33, Compound 34, Compound 35, Compound 36, Compound 37, Compound 38, Compound 39, Compound 40, Compound 41, Compound 42, Compound 43, Compound 44, Compound 45, Compound 46, Compound 47, Compound 48, Compound 49, Compound 50, Compound 51, Compound 52, Compound 53, Compound 54, Compound 55, Compound 56, Compound 57, Compound 58, Compound 59, Compound 60, Compound 61, Compound 62, Compound 63, Compound 64, Compound 65, Compound 66, Compound 67, Compound 68, Compound 69, Compound 70 and Compound 71.

In some embodiments, said compound is Compound 1 or Compound 2 or Compound 3 or Compound 4 or Compound 5 or Compound 6 or Compound 7 or Compound 8 or Compound 9 or Compound 45 or Compound 46 or Compound 47 or Compound 48 or Compound 49 or Compound 50 or Compound 54 or Compound 55 or Compound 56 or Compound 57 or Compound 58 or Compound 64 or Compound 65 or Compound 66 or Compound 67 or Compound 68.

The compounds of the invention may be generally formed by a two-step process, comprising:

(1) forming or obtaining a ligand, said ligand being defined as above; and (2) reacting said ligand with a suitable metal precursor, wherein said metal being titanium(IV), vanadium(V), oxovanadium(V), vanadium(IV), oxovanadium(IV); said metal precursor being optionally selected amongst titanium (IV) salts, vanadium (V) salts, oxovanadium (V) salts, vanadium (IV) salts and oxovanadium(IV) salts, respectively, depending on the selected metal.

In some embodiments, the titanium precursor is selected from $Ti(OR)_4$, $L_xTi(OR)_y$ complexes wherein x=1-3 and y=1-3; $TiCl_m$ wherein m=3-4; hydrated titania sols and others, wherein in the above R is selected from methyl, ethyl, propyl, and butyl and L is selected from acetylacetone, or similar bidentate or polydentate ligands.

In some embodiment, the vanadium precursor comprise is selected from ammonium metavanadate, vanadium pentoxide, vanadium tetraoxide, oxytrihalides, vanadium alkylcarboxylates, vanadium oxysulfate, oxyvanadium carboxylate salt, vanadium oxyacetylacetonate complex, and vanadic acid and other vanadium salts.

The invention further provides use of a metal complex of the invention for the preparation of a formulation for medicinal or non-medicinal use, the compound being a metal complex comprising a titanium atom or a vanadium atom covalently bound to a single polydentate ligand and optionally to no more than 1 labile monodentate group or an oxo group. In some embodiments, the formulation is not for use in catalysis ex-vivo.

Irrespective of the intended final use, a compound according to the invention may be formulated into a variety of formulations selected from liquid or solid or oil formulations, emulsions, dispersions, encapsulated in a variety of carriers or in liposomes, nanoparticles, microparticles, microcapsules and others relevant to medicinal uses.

In some embodiments, the compounds of the invention are suitable and effective when encapsulated in an inert or active coating material which permits controlled, slow or fast, short or long-term release of a compound of the invention. As used herein, the term "encapsulation" or any lingual variation thereof, means to encase a material of the invention in a shell material, e.g., a polymeric material, where the polymeric material may or may not be a product of polymerizing monomers in the presence of the compound of the invention when dispersed with a polymeric dispersant.

The encapsulating process may form spheres or capsules in which the material is encaged within the spheres or capsules or embedded within the spheres or capsules shell. The spheres have different diameters between as few nanometers to millimeters. The encapsulation process depends on the physical and chemical properties of the specific compound of the invention. Methods for encapsulation of compounds such as those of the invention using a variety of size particles or carriers have been described. Generally, encapsulation entails the formation of polymer particles of a variety of sizes including nanoparticles, microparticles, miliparticles, nanocapsules, microcapsules, milicapsules, nanoemulsions, microemulsions, nanospheres, microspheres, liposomes, oleosomes, vesicles, micelles, surfactants, phospholipids, sponges, and cyclodextrines.

The methods of encapsulating the compounds of the invention may include emulsion polymerization, interfacial polymerization, solvent evaporation, salting out, combination of sonication and layer-by-layer technology, and solvent displacement/solvent diffusion.

In some embodiments, the metal complex compounds of the invention are formed as nanoparticles or microparticles. In some embodiments, the nanoparticles are of a size (e.g., diameter) of between about 10 and 900 nm. In other embodiments, the nanoparticles are between about 100 and 900 nm. In other embodiments, the nanoparticles are between about 100 and 800 nm. In other embodiments, the nanoparticles are between about 100 and 700 nm. In other embodiments, the nanoparticles are between about 100 and 600 nm. In other embodiments, the nanoparticles are between about 100 and 500 nm. In other embodiments, the nanoparticles are between about 100 and 400 nm. In other embodiments, the nanoparticles are between about 100 and 300 nm. In other embodiments, the nanoparticles are between about 100 and 200 nm.

In other embodiments, the nanoparticles are between about 10 and 100 nm. In other embodiments, the nanoparticles are between about 10 and 90 nm. In other embodiments, the nanoparticles are between about 10 and 80 nm. In other embodiments, the nanoparticles are between about 10 and 70 nm. In other embodiments, the nanoparticles are between about 10 and 60 nm. In other embodiments, the nanoparticles are between about 10 and 50 nm. In other embodiments, the nanoparticles are between about 10 and 40 nm. In other embodiments, the nanoparticles are between about 10 and 30 nm. In other embodiments, the nanoparticles are between about 10 and 20 nm.

In other embodiments, the nanoparticles are between about 50 and 900 nm. In other embodiments, the nanoparticles are between about 50 and 800 nm. In other embodiments, the nanoparticles are between about 50 and 700 nm. In other embodiments, the nanoparticles are between about 50 and 600 nm. In other embodiments, the nanoparticles are between about 50 and 500 nm. In other embodiments, the nanoparticles are between about 50 and 400 nm. In other embodiments, the nanoparticles are between about 50 and 300 nm. In other embodiments, the nanoparticles are between about 50 and 200 nm. In other embodiments, the nanoparticles are between about 50 and 100 nm. In other embodiments, the nanoparticles are between about 50 and 90 nm. In other embodiments, the nanoparticles are between about 50 and 80 nm. In other embodiments, the nanoparticles are between about 50 and 70 nm. In other embodiments, the nanoparticles are between about 50 and 60 nm.

In other embodiments, the nanoparticles are between about 1 and 200 nm. In other embodiments, the nanoparticles are between about 1 and 100 nm. In other embodiments, the nanoparticles are between about 1 and 90 nm. In other embodiments, the nanoparticles are between about 1 and 80 nm. In other embodiments, the nanoparticles are between about 1 and 70 nm. In other embodiments, the nanoparticles are between about 1 and 60 nm. In other embodiments, the nanoparticles are between about 1 and 50 nm. In other embodiments, the nanoparticles are between about 1 and 40 nm. In other embodiments, the nanoparticles are between about 1 and 30 nm. In other embodiments, the nanoparticles are between about 1 and 20 nm. In other embodiments, the nanoparticles are between about 1 and 10 nm. In other embodiments, the nanoparticles are about 1, or 2 or 3 or 4 or 5 or 6 or 7 or 8 or 9 or 10 or 11, or 12, or 13 or 14 or 15 nm in size (diameter).

The nano- or micro-particles are typically spherical in shape. Where the nanoparticles are different from spheres, the size is of the longest axis. The nanoparticles sizes provided herein are averaged.

In some embodiments, the compounds of the invention are formulated as nanoparticles.

In some embodiments, the use of any one or more compound of the invention in catalysis is excluded. In some embodiments, the metal complexes of the invention are not for use as catalysts. In some embodiments, the metal complexes of the invention are not for use as catalysts in any one chemical transformation. In further embodiments, the metal complexes of the invention are not for use as catalysts in chemical transformations carried out ex-vivo. In some embodiments, the compound excluded for use in catalysis is Compound 1 or Compound 2 or Compound 3 or Compound 4 or Compound 5 or Compound 6 or Compound 7 or Compound 8 or Compound 9 or Compound 10 or Compound 11 or Compound 12 or Compound 13 or Compound 14 or Compound 15 or Compound 16 or Compound 17 or Compound 18 or Compound 19 or Compound 20 or Compound 21 or Compound 22 or Compound 23 or Compound 24 or Compound 25 or Compound 26 or Compound 27 or Compound 28 or Compound 29 or Compound 30 or Compound 31 or Compound 32 or Compound 33 or Compound 34 or Compound 35 or Compound 36 or Compound 37 or Compound 38 or Compound 39 or Compound 40 or Compound 41 or Compound 42 or Compound 43 or Compound 44 or Compound 45 or Compound 46 or Compound 47 or Compound 48 or Compound 49 or Compound 50 or Compound 51 or Compound 52 or Compound 53 or Compound 54 or Compound 55 or Compound 56 or Compound 57 or Compound 58 or Compound 59 or Compound 60 or Compound 61 or Compound 62 or Compound 63 or Compound 64 or Compound 65 or Compound 66 or Compound 67 or Compound 68 or Compound 69 or Compound 70 or Compound 71.

In other embodiments, the compounds of the invention are formed into a composition or a formulation, wherein the compound formulated is not Compound 1 or Compound 2 or Compound 3 or Compound 4 or Compound 5 or Compound 6 or Compound 7 or Compound 8 or Compound 9 or Compound 10 or Compound 11 or Compound 12 or Compound 13 or Compound 14 or Compound 15 or Compound 16 or Compound 17 or Compound 18 or Compound 19 or Compound 20 or Compound 21 or Compound 22 or Compound 23 or Compound 24 or Compound 25 or Compound 26 or Compound 27 or Compound 28 or Compound 29 or Compound 30 or Compound 31 or Compound 32 or Compound 33 or Compound 34 or Compound 35 or Compound 36 or Compound 37 or Compound 38 or Compound 39 or Compound 40 or Compound 41 or Compound 42 or Compound 43 or Compound 44 or Compound 45 or Compound 46 or Compound 47 or Compound 48 or Compound 49 or Compound 50 or Compound 51 or Compound 52 or Compound 53 or Compound 54 or Compound 55 or Compound 56 or Compound 57 or Compound 58 or Compound 59 or Compound 60 or Compound 61 or Compound 62 or Compound 63 or Compound 64 or Compound 65 or Compound 66 or Compound 67 or Compound 68 or Compound 69 or Compound 70 or Compound 71.

In some embodiments, the compound is not Compound 63. In some embodiments, the compound is not an oxovanadium complex of L63.

The invention further provides a compound for use in medicine, i.e., for use in a method of treatment or prevention of a disease or disorder in a human or non-human animal, said compound being of any of the above formulae. In some embodiments, the compound for use in medicine is one or more of compounds herein designated Compound 1 or Compound 2 or Compound 3 or Compound 4 or Compound 5 or Compound 6 or Compound 7 or Compound 8 or Compound 9 or Compound 10 or Compound 11 or Compound 12 or Compound 13 or Compound 14 or Compound 15 or Compound 16 or Compound 17 or Compound 18 or Compound 19 or Compound 20 or Compound 21 or Compound 22 or Compound 23 or Compound 24 or Compound 25 or Compound 26 or Compound 27 or Compound 28 or Compound 29 or Compound 30 or Compound 31 or Compound 32 or Compound 33 or Compound 34 or Compound 35 or Compound 36 or Compound 37 or Compound 38 or Compound 39 or Compound 40 or Compound 41 or Compound 42 or Compound 43 or Compound 44 or Compound 45 or Compound 46 or Compound 47 or Compound 48 or Compound 49 or Compound 50 or Compound 51 or Compound 52 or Compound 53 or Compound 54 or Compound 55 or Compound 56 or Compound 57 or Compound 58 or Compound 59 or Compound 60 or Compound 61 or Compound 62 or Compound 63 or Compound 64 or Compound 65 or Compound 66 or Compound 67 or Compound 68 or Compound 69 or Compound 70 or Compound 71.

In some embodiments, the compounds of the invention are used as cytotoxic agents and/or as anti-angiogenesis agents and/or anti-cancer agents.

As stated herein, the metal complex compounds of the invention may be administered directly without a further hydrolysis step. As above, the solubility and cell-penetration characteristics of the compounds may be modifiable by reducing their particle size to the nanoscale. Thus, in some cases, the compounds may be formulated or nano-formed in order to facilitate a more efficient administration thereof to a subject requiring treatment therewith. The compounds of the invention may be formulated into various formulation or compositions for a variety of uses. In some embodiments, the compounds are formulated as pharmaceutical compositions for therapeutic use.

Thus, also contemplated are pharmaceutical compositions comprising a compound of any one or more formula according to the invention, e.g., formula (I) or formula (Ia) or formula (II) or formula (IIa) or formula (IIb) or formula (IIc) or formula (IId) or formula (IIe) or formula (IIf) or formula (IIg) or formula (III) or formula (IV) or formula (IVa) or formula (IVb), as defined hereinabove, as disclosed herein.

In some embodiments, the pharmaceutical compositions of the invention comprise at least one compound selected from Compound 1 through Compound 71. In some embodiments, the composition comprises any one compound listed in Table 1.

For the sake of brevity, embodiments disclosed herein with respect to compounds of the invention are incorporated herein with respect to each of the therapeutic aspects disclosed herein.

In some embodiments, the pharmaceutical composition is for use in the treatment or prevention of a disease or disorder.

In some embodiments, the compositions are pharmaceutical compositions, optionally comprising also a pharmaceutically acceptable carrier, diluents or excipient. As known in the art, the pharmaceutically acceptable carrier, diluents or excipient is selected to be chemically inert to the active compounds contained in the composition of the invention (i.e., alone or in combination) and one which has no detrimental side effects or toxicity under the conditions of use.

The choice of carrier will be determined in part by the particular compound of the invention, or combinations thereof, as well as by the particular method used to administer the composition. Accordingly, there is a wide variety of suitable formulations of the pharmaceutical composition of the present invention. The following formulations for oral, aerosol, parenteral, subcutaneous, intravenous, intramuscular and interperitoneal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the metal complex, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent.

Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The metal complexes of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. The metal complex can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-β-aminopriopionates, and 2-alkyl-imidazoline quaternary ammonium salts, and (3) mixtures thereof.

The parenteral formulations may contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The metal complexes of the present invention may be made into injectable formulations. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, eds., pages 238-250 (1982), and *ASHP Handbook on Injectable Drugs*, Toissel, $4^{th}$ ed., pages 622-630 (1986).

Additionally, the metal complexes of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the metal complex, such carriers as are known in the art to be appropriate.

Generally, the pharmaceutical composition of the invention is suitable for use in the treatment or prevention of a disease or disorder. In some embodiments, such disease or disorder is a malignant proliferative condition.

As used herein, the term "malignant" refers to a severe and progressively worsening disease state. The term malignant is typically used to describe cancer. Thus, malignancy, as in malignant neoplasm, and malignant tumor, are used synonymously with cancer, and also prefix other oncology terms such as malignant ascites, and malignant transformation.

In another aspect, the invention provides a method for treating or preventing a disease or disorder in a subject suffering therefrom or having genetic or environmental predisposition to suffering from said disease or disorder, said method comprising administering a compound of the invention, as described hereinabove. In some embodiments, said compound is at least one compound selected from Compound 1 through Compound 71.

It is a further aspect of the invention to provide a method for treating or preventing cancer in a subject suffering therefrom or having genetic or environmental predisposition to suffering from cancer, said method comprising administering an effective amount of a compound of the invention, as disclosed hereinabove.

In some embodiments, said cancer is a multi-drug resistant (MDR) cancer. In such embodiments, said MDR cancer may be resistant to cis-platin.

When employed in a method according to the invention, the metal complex compounds of the invention can be used to treat a wide spectrum of cancers (neoplasms), such as blastoma, carcinoma, lymphoma, including: Hodgkin's and non-Hodgkin's lymphoma, leukemia, leukemia myeloma, sarcoma, mesothelioma, glioma, germinoma, choriocarcinoma, melanoma, glioblastoma, lymphoid malignancies and any other neoplastic disease or disorder.

Non-limiting examples of cancer which can be treated using the compounds according to invention include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Also included are solid cancers such as breast cancer, prostate cancer, sarcomas, and skin cancer.

In some embodiments, the cancer to be treated by the compounds/compositions of the invention is ovarian or colon cancer.

In yet another aspect of the invention there is provided a method for treating or preventing a disease or disorder in a subject suffering therefrom or having genetic or environmental predisposition to suffer from said disease or disorder, said method comprising administering a compound of any of the formulae disclosed hereinabove.

The term "treatment" as used herein refers to the administering of a therapeutic amount of a metal complex or a composition comprising same according to the present invention which is effective to ameliorate undesired symptoms associated with a disease, e.g., a malignancy, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease from occurring or a combination of two or more of the above.

To achieve treatment and/or prevention of a disease or disorder treatable by a compound according to the invention, the compound may be administered in an amount which is effective in achieving the desired treatment or prevention. The "effective amount" for purposes herein is determined by such considerations as may be known in the art. The amount must be effective to achieve the desired therapeutic effect as described above, i.e. treat or prevent malignancies, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half life in the body, on undesired side effects, if any, on factors such as age and gender, etc.

The invention further provides the use of a compound as hereinabove described in the preparation of a pharmaceutical composition for the treatment of a disease or disorder. In such embodiments, said disease may be cancer.

In another one of its aspects, there is provided the use of a compound of the invention in a method of treatment or prophylaxis of a disease or disorder. In such embodiments, said disease may be cancer.

In a further aspect of the invention, there is provided a kit comprising the compound of any one of the formulae disclosed hereinabove, or the pharmaceutical composition comprising same, as hereinabove described, and instructions for use.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

As noted hereinabove, titanium(IV) based anticancer complexes were the first to enter clinical trials following platinum compounds, demonstrating high antitumor activity toward a range of cancer cells with reduced toxicity. The recently introduced cytotoxic bis(alkoxo)salan $Ti^{IV}$ complexes had been determined to be: (a) substantially more hydrolytically stable than known $Ti^{IV}$ complexes; and (b) markedly more active than (bzac)$_2$Ti(OiPr)$_2$, Cp$_2$TiCl$_2$, and cis-platin toward variety of cancer-derived cell lines. Nevertheless, these complexes ultimately hydrolyzed to release the labile alkoxo ligands in the biological environment to give polynuclear products. These products although were inactive when administered directly, surprisingly showed high cytotoxicity when formulated into nano-particles.

Vanadium complexes have also previously been shown to lead to cytotoxic compounds. Vanadium(V) complexes based on salan ligands with a labile alkoxo group showed high cytotoxicity but low stability in water.

Herein, the inventors of the present application describe a novel approach which stands against the presently acceptable notion that labile groups are necessary for increased cytotoxicity and provide support to the fact that labile ligands are not be required for cytotoxicity of Ti and V complexes unlike for cis-platin.

It has also been found that reducing the particle size of the complexes of the invention to the nanometric range accelerated intercellular permeability, increased solubility and the dissolution rate. Nanoparticles of Ti and V complexes of the invention were obtained by a rapid conversion of a volatile oil-in-water microemulsion into a dry powder composed of nanoparticles. Rapid evaporation of the volatile droplets containing the complex yielded the powder, which was easily dispersible in an aqueous medium to form stable nanometric dispersions. Notably, the surfactants used were approved by FDA for incorporation into pharmaceutical dosage forms.

Under the notion that labile ligands were not essential for cytotoxicity, pre-designed inert and hydrolytically stable cytotoxic complexes are highly advantageous because the hydrolysis step and the accompanying undesired release of side products such as free labile ligands are eliminated. Thus, tris- and tetrakis-phenolato ligands were prepared and afforded the monomeric octahedral complexes compound 3 and compound 4 (Scheme 2).

Scheme 2

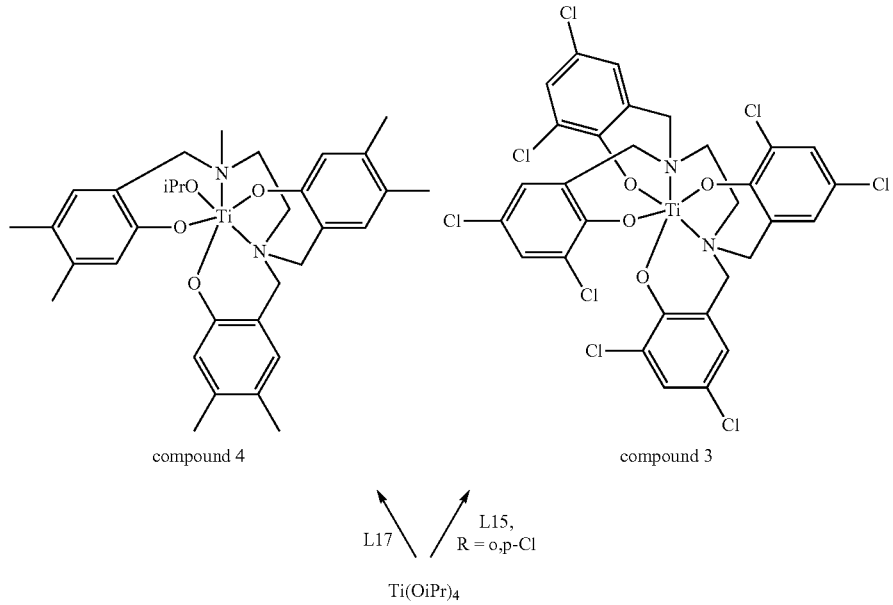

compound 4    compound 3

L17  L15, R = o,p-Cl

Figure 1:
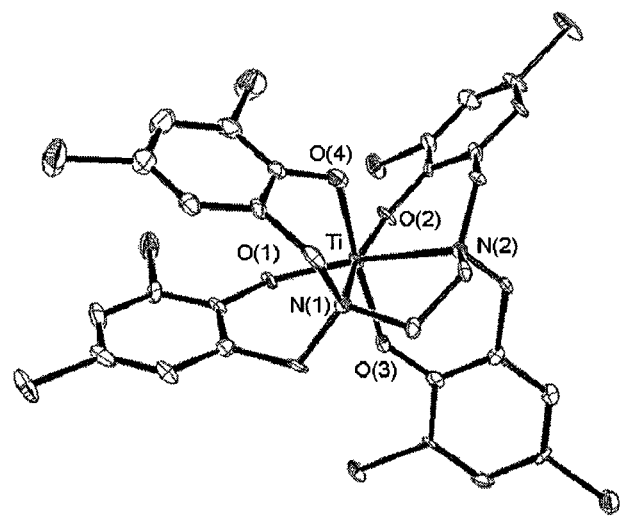
FIG. 1 present the ORTEP drawings of compound 3 in 50% probability ellipsoids; H-atoms and solvent molecule were omitted for clarity.

Ti(OiPr)$_4$ $^1$H NMR confirmed that a single product of each complex had formed and the X-ray structure of compound 3 featured an octahedral C$_2$-symmetrical complex (FIG. 1).

TABLE 2

Mean particle size measured for 0.2 wt % dispersion in water and IC$_{50}$ (μM) values toward OVCAR and HT-29 cancer cells for the nanoformulated complexes of the invention.

| Complex | Particle size (nm) | OVCAR (μM) | HT-29 (μM) | HU-2 (μM) |
|---|---|---|---|---|
| compound 4 | 9.0 ± 0.6 | 70 ± 22 | 54 ± 16 | |
| compound 3 | 5.3 ± 0.3 | 14 ± 4 | 12 ± 2 | 0.8 ± 1 |

Comparative hydrolysis measurements by $^1$H NMR were carried by monitoring the integration of selected signals with time following addition of 10% D$_2$O to [D8]THF solution of the complexes. The $t_{1/2}$ value for isopropoxo hydrolysis for compound 4 was ca. 100 hours, markedly higher than the value previously reported for analogous complexes of two labile ligands obtained under similar conditions (ca. 5 hours). Compound 3 demonstrated even higher stability, where no substantial hydrolysis was observed for over a week. As expected, the decrease in the number of labile ligands dramatically increased the hydrolytic stability of the complexes.

Figure 2:
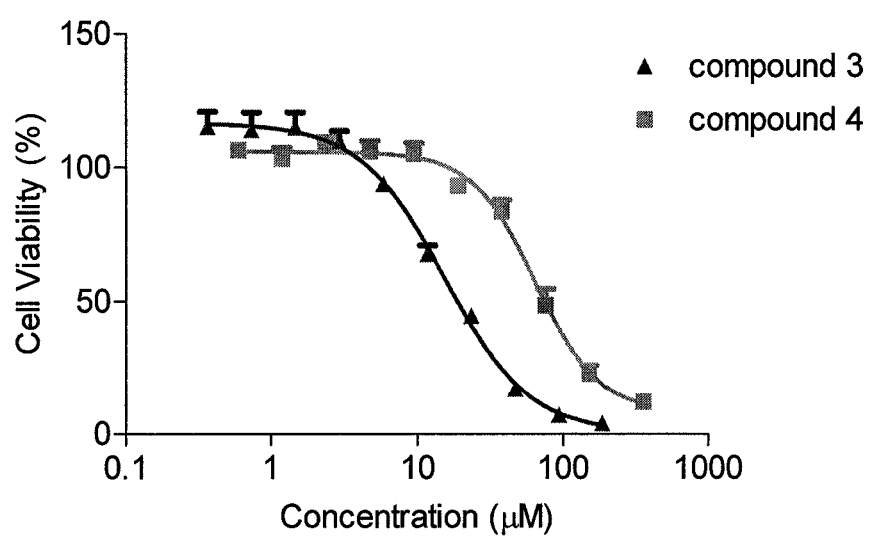
FIG. 2 depicts dependence of OVCAR cell viability following a three days incubation period on administered concentration of compound 3, compound 4 and the hydrolysis product of compound 4 administered in a nanoformulated form.

Compound 3, compound 4, and the hydrolysis product of compound 4 were all inactive when measured directly on HT-29 and OVCAR-1 cells. However, when formulated into nanoparticles, both were cytotoxic (FIG. 2, Table 2). Particularly, the most stable complex compound 3 exhibited the highest cytotoxicity, with $IC_{50}$ values that are comparable to those of the most active salan bis(alkoxo) derivatives. Additionally, compound 3 also showed particularly high cytotoxicity toward the multi-drug-resistant (MDR) cells HU-2.

Figure 3A:
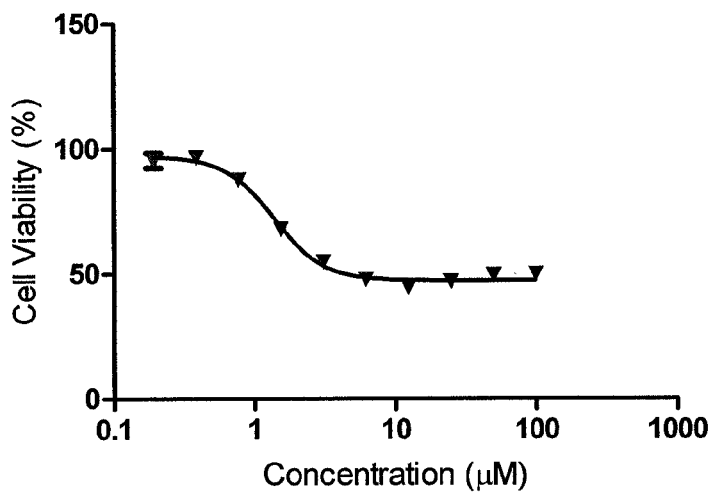
FIGS. 3A-B depict dependence of HT-29 cell viability following a three days incubation period on administered concentrations of compound 1 (FIG. 3A) and compound 2 (FIG. 3B).
Figure 3B:
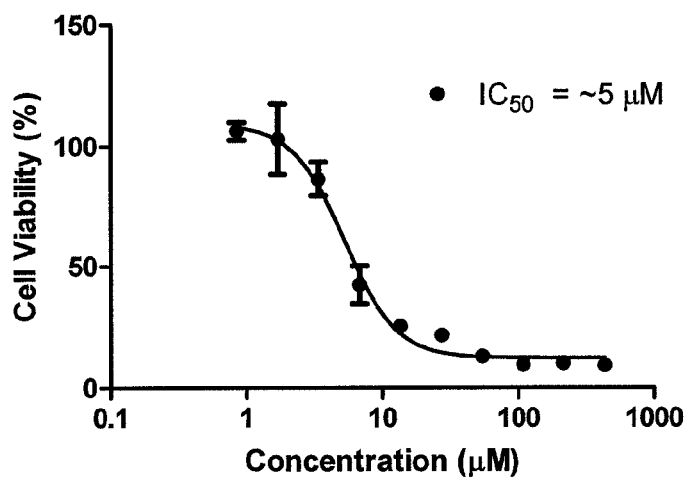

Compound 1 and compound 2 were synthesized similarly. Importantly, these complexes showed cytotoxic activity independent of formulations, even when administered directly (FIGS. 3A-B). The hydrolytic stability of these complexes is similarly high, where no decomposition is observed for days in water solutions.

Figure 4A:
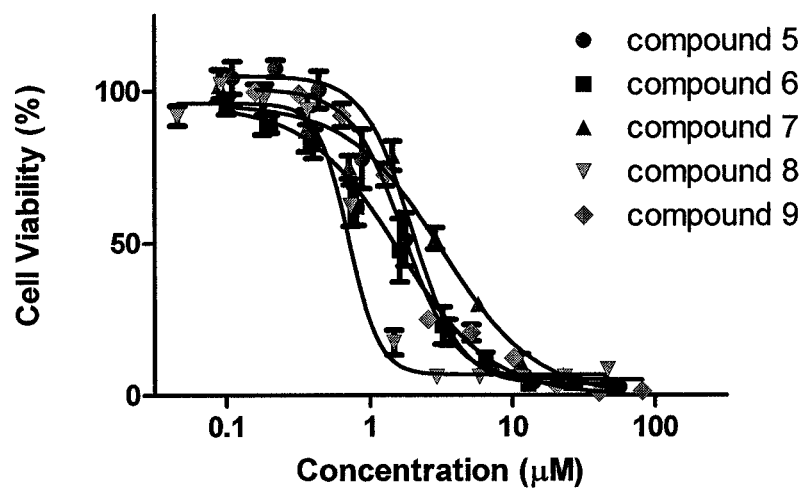
FIGS. 4A-B depict dependence of HT-29 (FIG. 4A) and OVCAR-3 (FIG. 4B) cell viability following a three days incubation period on administered concentrations of compounds 5-9.
Figure 4B:
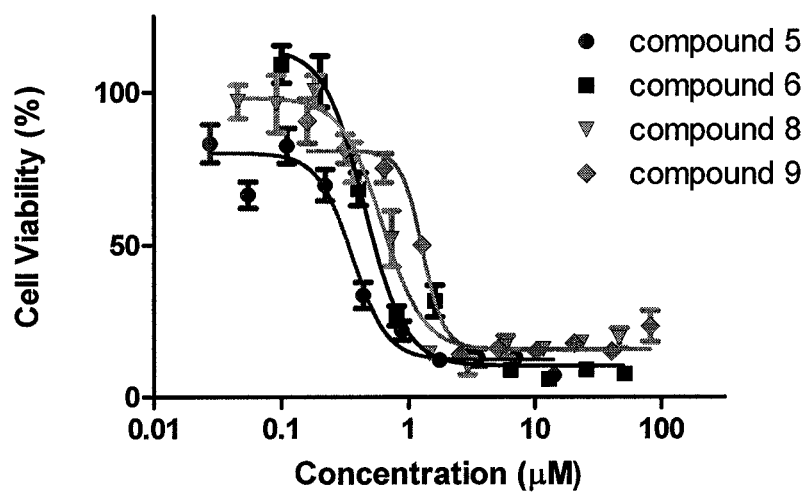

FIGS. 4A-B depict dependence of HT-29 (FIG. 4A) and OVCAR-3 (FIG. 4B) cell viability following a three days incubation period on administered concentrations of compounds 5-9.

Similar results have been obtained for the various vanadium(V) complexes of the invention. Ligands were generally prepared according to known procedures, and the complexes were obtained by reacting the ligands with a vanadium precursor under inert conditions and possibly with the addition of base. As demonstrated in Table 3, vanadium complexes compounds 5-9 exhibited a remarkable cytotoxic activity which is significantly higher than that of cis-platin toward ovarian and colon cells. These vanadium complexes with no labile ligands demonstrated the activity also when administered directly, independent of particular formulations. Moreover, these complexes are stable for weeks in the presence of water.

Figure 5:
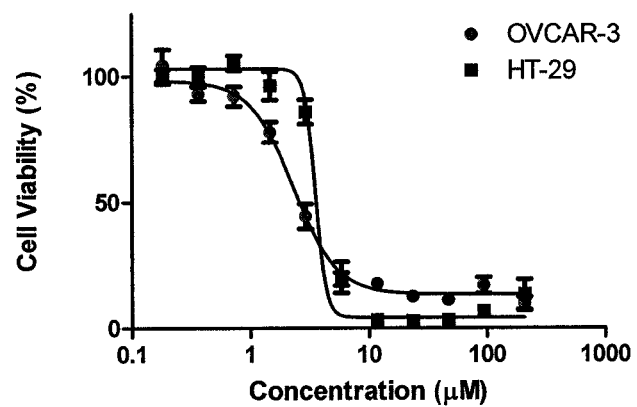
FIG. 5 depicts dependence of HT-29 and OVCAR-3 cell viability following a three days incubation period on administered concentrations of compound 50.
Figure 6:
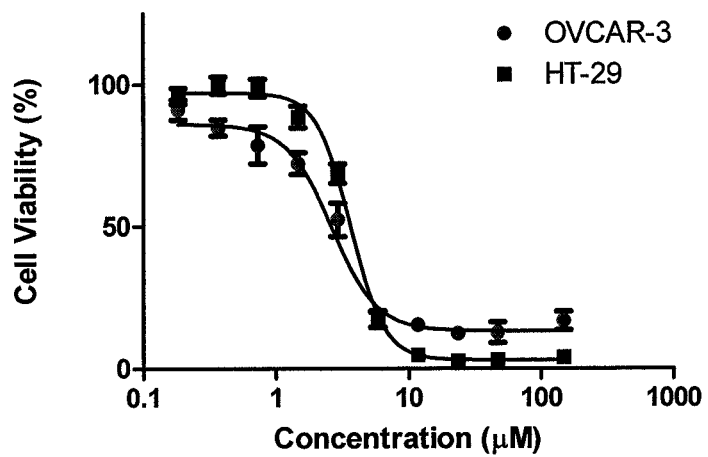
FIG. 6 depicts dependence of HT-29 and OVCAR-3 cell viability following a three days incubation period on administered concentrations of compound 63.

The vanadium(V) complex compound 50 (FIG. 5) and the vanadium(IV) complex compound 63 (FIG. 6) also showed high activity independent of formulations (Table 3).

Figure 7A:
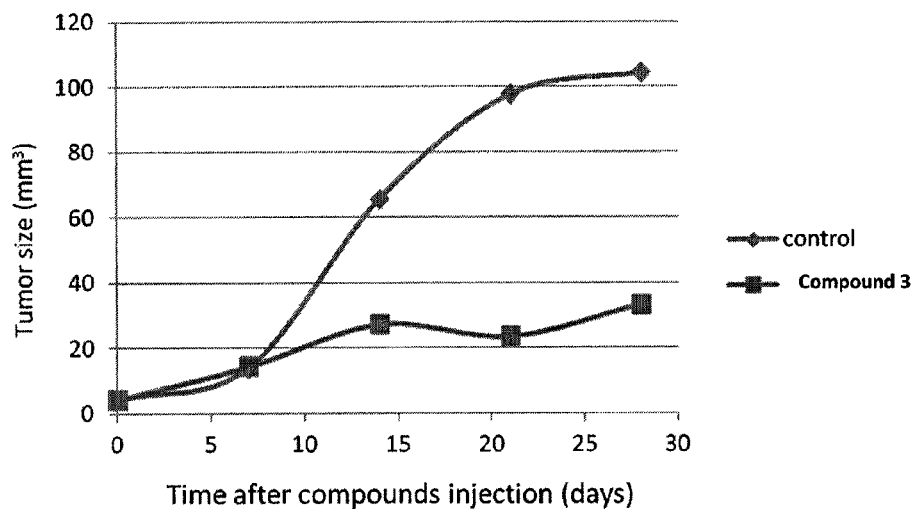
FIGS. 7A-B depict dependence of average tumor size on time following administration of compound 3 (FIG. 7A) and compound 5 (FIG. 7B): 100 μg per mouse per injection, IP, every other day for 4 weeks, to a group of 5 mice previously treated with HT-29-human colon adenocarcinoma (5*10$^6$ cells, SC) relative to untreated control.
Figure 7B:
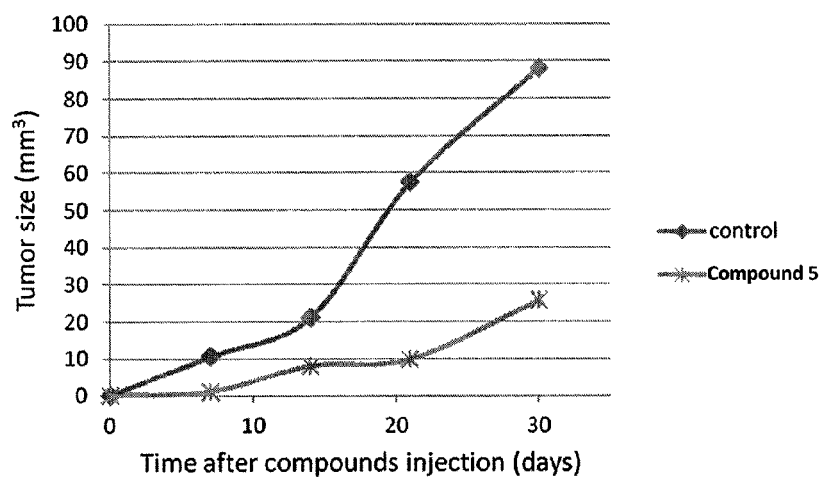

FIGS. 7A-B depict dependence of average tumor size on time following administration of compound 3 (FIG. 7A) and compound 5 (FIG. 7B): 100 μg per mouse per injection, IP, every other day for 4 weeks, to a group of 5 mice previously treated with HT-29-human colon adenocarcinoma ($5*10^6$ cells, SC) relative to untreated control.

TABLE 3

Cytotoxic activity of vanadium complexes of the invention administered without formulations as compared to cis-platin.

| Complex | IC50 and maximal inhibition values | |
|---|---|---|
|  | OVCAR-3 | HT-29 |
| Cis-platin | 8.8 ± 2.1 (91%) | 12.2 ± 2.3 (90%) |
| compound 5 | 0.3 ± 0.1 (88%) | 1.9 ± 0.6 (97%) |
| compound 6 | 0.3 ± 0.1 (90%) | 2.5 ± 0.7 (98%) |
| compound 7 |  | 3.2 (95%) |
| compound 8 | 0.6 ± 0.2 (85%) | 0.7 ± 0.1 (94%) |
| compound 9 | 1.3 (84%) | 2.0 ± 0.4 (99%) |
| compound 50 | 2.8 ± 0.5 (87%) | 4.6 ± 0.8 (96%) |
| compound 63 | 4.3 ± 1.4 (87%) | 5.8 ± 0.3 (97%) |

The results presented herein attest to the ability of the biologically friendly Ti species to form complexes that are stable for weeks in an aqueous environment and are highly cytotoxic. Similarly, vanadium complexes can also demonstrate this desired combination of features. The results presented herein provide a well-established understanding that unlike for cis-platin, ligand lability is not a pre-requisite for cytotoxicity of Ti and V complexes, which serves as a particular advantage in this case due to the rich aquatic chemistry of Ti and V compounds. Thus, stable Ti and V complexes are certainly attainable and may lead to high activity in a controlled manner without accompanying release of undesired products. For this reason, administering the stable active species directly is advantageous over receiving it through a hydrolysis step.

Ligands and complexes were generally synthesized according to published procedures. All ligands were dried at ~80° C. under vacuum for over 12 hours before complexation. All solvents were distilled using K or K/benzophenone under nitrogen, or dried over aluminum column on an M. Braun drying system SPS-800. All experiments requiring dry atmosphere were performed in an M. Braun dry-box or under nitrogen atmosphere using Schlenck line techniques.

Microemulsions were prepared by dissolving Ti or V complexes in n-butyl acetate (purchased from Sigma-Aldrich Chemical Company Inc.) and adding soybean phosphatidylcholine (at least 92% purity, Lipoid S75, supplied by Lipoid, Switzerland), ammonium glycyrrhizinate (purchased from Sigma-Aldrich Chemical Company Inc), dipotassium glycyrrhizinate (obtained from TCI, Japan) and isopropyl alcohol (purchased from Sigma-Aldrich Chemical Company Inc.) to the resultant solution as to create an oil phase. Water was then added and the mixture and was allowed to equilibrate at 25° C. until transparent isotropic system was formed.

Microemulsion compositions used as templates for the nanopowder preparation were: Ti complex 1.5 wt %, n-butyl acetate (volatile solvent) 23.5 wt %, isopropyl alcohol 25 wt %, ammonium glycyrrhizinate (surfactant) 6 wt %, soybean phosphatidylcholine (surfactant) 4 wt %, dipotassium glycyrrhizinate (surfactant) 5 wt % and water 35 wt %. The resultant system was homogeneous, optically transparent and exhibited no birefringence.

All solvents were evaporated from the microemulsion at a temperature of −47±3° C. and absolute pressure <1 mbar using a DW-3 Lyopholizer (Heto-Drywinner, Denmark). The samples were kept under these conditions for 72 hours. Dry solvent-free powders were consequently obtained. The composition of these powders was: salan TiIV complex 9.1 wt %, ammonium glycyrrhizinate 36.4 wt %, soybean phosphatidylcholine 24.2 wt %, dipotassium glycyrrhizinate 30.3 wt %.

The dry powder obtained at the end of the freeze-drying process was dispersed at 0.2% in distilled water. The sample was manually shaken for 15 seconds. Particle size distribution by volume was measured at room temperature by dynamic light scattering using a Nano-ZS Zetasizer (Malvern, UK). A 633 nm wavelength laser beam was used to illuminate the sample and the light scattering was detected at 173° angle by the Non-Invasive Back-Scatter (NIBS) technology. The advantages of the backscatter detection are: (a) Ability to measure particle size at high concentration; (b) Elimination of dust and impurity effect. Size measurements of the dispersion were performed in triplicate.

As a reference, nanopowder without the complexes was prepared similarly, dispersed in water, and the particle size was 4.9±0.2 nm, much smaller than that of the nanoparticles with the reagent tested.

NMR data were recorded using AMX-400 or AMX-500 MHz Bruker spectrometer. X-ray diffraction data were obtained with a Bruker SMART APEX CCD diffractometer, running the SMART software package. After collection, the raw data frames were integrated by the SAINT software package. The structures were solved and refined using the SHELXTL software package. Hydrolysis studies by NMR were performed using a solution of the complex in $[D^8]THF$ and adding 10% $D_2O$. The results were verified by including p-dinitrobenzene as an internal standard.

Cytotoxicity was measured on HT-29 colon and OVCAR ovarian cells obtained from ATCC Inc. using the methylthiazolyldiphenyl-tetrazolium bromide (MTT) assay. Cells ($0.6 \times 10^6$) in medium (contains: 1% penicillin/streptomycin antibiotics; 1% L-glutamine; 10% fetal bovine serum (FBS) and 88% medium RPMI-1640, all purchased from Biological Industries Inc.) were seeded into a 96-well plate and allowed to attach for a day. The cells were consequently treated with the reagent tested at 10 different concentrations. Solutions/dispersions of the reagents were prepared either by dissolving 8 mg of the nonformulated reagent in 200 μL of THF or by dispersing 8 mg of formulated reagent in 200 μL of medium, with further diluting to obtain the different concentrations. A total of 20 μL of the resulting system were diluted with 180 μL of medium. Consequently, 10 μL of each final system were added to each well already containing 200 μL of the above solution of cells in the medium to give final concentration of up to 200 mg/L. Control wells were treated with similar amounts of THF or medium. After a standard of 3 days incubation at 37° C. in 5% $CO_2$ atmosphere, MTT (0.1 mg in 20 μL) was added and the cells were incubated for additional 3 hours. The MTT solution was then removed, and the cells were dissolved in 200 μL isopropanol. The absorbance at 550 nm was measured by a Bio-Tek EL-800 microplate reader spectrophotometer. Each measurement was repeated at least 3×3 times, namely, three repeats per plate, all repeated at least 3 times on different days (9 repeats altogether). $IC_{50}$ values were determined by a non-linear regression of a variable slope (four parameters) model.

All ligands have been prepared following published or modified procedures. Ligand L5 was obtained based on a published procedure [27].

Ligand L6 was obtained by reacting one equivalent of N,N'-Bis(2-hydroxyethyl) ethylenediamine with two equivalents of 2-hydroxy-5-nitrobenzyl bromide and five equivalents of triethylamine in THF. The reaction was stirred overnight and the precipitate formed was expelled by filtration. The filtrate was evaporated and the product was obtained as a yellow powder after recrystallized in ethanol.

Ligand L17 was synthesized by refluxing 3,4-dimethylphenol (2.44 g, 20 mmol) with formaldehyde (4 ml, 40 mmol) and N-methylethylenediamine (0.58 ml, 6.67 mmol) for 24 hours in methanol (20 ml). The solution was allowed to cool to room temperature and the colorless precipitate was collected by filtration to produce the ligand in 40% yield.

$^1$H NMR (400 MHz, $CDCl_3$): δ=6.77 (s, 2H; Ar), 6.68 (s, 1H; Ar), 6.63 (s, 1H; Ar), 6.59 (s, 2H; Ar), 3.62 (s, 4H; CH2), 3.58 (s, 2H; CH2), 2.71 (t, J=3.6 Hz, 2H; CH2), 2.68 (t, J=3.6 Hz, 2H; CH2), 2.22-2.08 ppm (m, 21H; CH3); 13C NMR (100 MHz; $CDCl_3$): δ=155.5, 154.0, 137.5, 137.2, 131.5, 130.1, 127.6, 127.1, 119.6, 119.1, 117.8, 117.7, 61.2, 55.7, 53.6, 50.6, 41.6, 19.7, 18.8 ppm; Anal. Calcd for $C_{30}H_{40}N_2O_3$: C, 75.59; H, 8.46; N, 5.88. Found: C, 75.40; H, 8.50; N, 5.80.

Compound 4 was synthesized by mixing $Ti(OiPr)_4$ (0.050 g, 0.18 mmol) dissolved in dry THF (5 ml) with L17 (0.072 g, 0.18 mmol) dissolved in dry THF (5 ml) under an inert atmosphere. The two solutions were allowed to mix at room temperature for 2 hours. The solvent was removed under reduced pressure to give the product as a yellow solid in a quantitative yield.

$^1$H NMR (400 MHz, $CDCl3$): δ=6.90 (s, 1H; Ar), 6.84 (s, 1H; Ar), 6.66 (s, 1H; Ar), 6.65 (s, 1H; Ar), 6.47 (s, 1H; Ar), 6.44 (s, 1H; Ar), 4.95 (sept, J=6.0 Hz, 1H; CHCH3), 4.61 (d, J=13.2 Hz, 2H; CH2), 4.41 (d, J=12.6 Hz, 1H; CH2), 3.40 (d, J=13.6 Hz, 1H; CH2), 3.37 (d, J=13.6 Hz, 1H; CH2), 3.03 (dt, J=14.0, 4.4 Hz, 1H; CH2), 2.73 (d, J=12.6 Hz, 1H; CH2), 2.49 (dt, J=12.6, 4.4 Hz, 1H; CH2), 2.26 (dd, J=14.0, 4.4 Hz, 1H; CH2), 2.23-2.09 (m, 21H; CH3), 1.78 (dd, J=14.0, 4.4 Hz, 1H; CH2), 1.23 (d, J=6.0 Hz, 3H; CHCH3), 1.22 ppm (d, J=6.0 Hz, 3H; CHCH3); 13C NMR (125 MHz; $CDCl3$): δ=161.1, 160.4, 160.2, 138.7, 138.2, 137.2, 131.0, 130.6, 130.4, 126.8, 126.0, 125.9, 122.0, 121.9, 121.4, 118.6, 118.0, 117.3, 78.8, 66.0, 65.1, 64.1, 59.3, 50.9, 44.2, 25.5, 25.5, 20.1, 19.9, 19.8, 19.0, 19.0 ppm; Anal. Calcd for $C_{33}H_{44}N_2O_4Ti$: C, 68.27; H, 7.64; N, 4.83. Found: C, 68.04; H, 7.55; N, 4.69.

Compound 3 was synthesized similarly, by reacting $Ti(OiPr)_4$ (0.050 g, 0.18 mmol) with L15 (R=o,p-Me) (0.126 g, 0.18 mmol) in dry THF under an inert atmosphere.

$^1$H NMR (500 MHz, [D8]THF): δ=7.32 (d, J=2.5 Hz, 2H; Ar), 7.27 (d, J=2.5 Hz, 2H; Ar), 7.14 (d, J=2.5 Hz, 2H; Ar), 6.90 (d, J=2.5 Hz, 2H; Ar), 4.66 (d, J=13.5 Hz, 2H; CH2), 3.91 (d, J=14.0 Hz, 2H; CH2), 3.73 (d, J=14.0 Hz, 2H; CH2), 3.67 (d, J=14.0 Hz, 2H; CH2), 2.97 (m, 4H; $CH_2$); 13C NMR (125 MHz; [$D_8$]THF): δ=157.4, 155.9, 130.3, 130.1, 129.6, 129.3, 128.3, 128.2, 125.5, 124.2, 123.0, 122.7, 66.1, 61.4, 59.4 ppm; Anal. Calcd for $C_{30}H_{20}Cl_8N_2O_4Ti$: C, 44.82; H, 2.51; N, 3.48. Found: C, 44.71; H, 3.02; N, 4.05.

Crystal data for compound 3: $C_{30}H_{20}Cl_8N_2O_4Ti \cdot 0.5 (C_7H_8)$, M=846.02, Triclinic, a=8.701(2), b=9.167(2), c=22.742(4) Å, α=80.004(3), β=85.872(3), γ=77.098(3)°. V=1740.1(5) Å$^3$, T=173(1) K, space group P, Z=2, μ(MoKα)=0.902 mm-1, 18949 reflections measured, 7523 unique ($R_{int}$=0.1017), R(F.° 2) for [I>2σ(I)]=0.1149, $R_w$ for [I>2σ(I)]=0.2190.

Compound 1 and compound 2 were obtained similarly by reacting one equivalent of the ligand L6 and L5, respectively, with one equivalent of $Ti(OiPr)_4$ in THF at room temperature under nitrogen atmosphere for several hours. The product precipitated from the solution and was isolated by decantation.

Ligands L7-L11 were prepared by modifying a previously published procedure [28]. Salicylaldehyde (or a substituted salicylaldehyde) was reacted in a 2:1 ratio with ethylene diamine and reduced with sodium borohydride to produce a salan compound. This compound was refluxed with an equimolar amount of the corresponding salicylaldehyde, and reduced with sodium borohydride to give the pentadentate tris(phenolato) ligand. The ligand was purified by extraction with ethyl acetate and crystallization from cold methanol.

Compound 5-9 were prepared by reacting equimolar amounts of Vanadium(V) trisisopropoxide oxide and the pentadentate tris(phenolato) ligand L7-L11, respectively.

Ligand L50 was synthesized according to a previously published procedure [29]. 2,4-dimethylphenol was heated with hexamethylenetetramine in the presence of p-toluene-sulfonic acid for 2 days. The resulting ligand was crystallized from cold methanol.

Compound 50: The complex was prepared by reacting equimolar amounts of Vanadium(V) trisisopropoxide oxide and the tetradentate tris(phenolato) ligand L50 in the presence of catalytic amount of triethylamine.

Ligand L63 was synthesized according to a previously published procedure [30].

Compound 63 was prepared as described previously [31]. Ligand L63 was reacted with equimolar amounts of $VOSO_4 \cdot 5H_2O$ in an aquatic solution, in the presence of sodium acetate to receive the required complex, which was collected by filtration.

The invention claimed is:
1. A metal complex selected from:
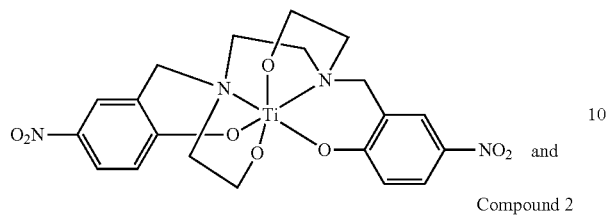
Compound 1
and
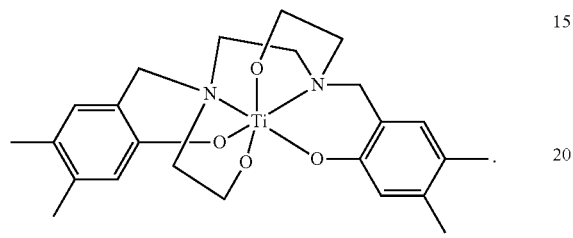
Compound 2
.
2. A composition comprising a metal complex according to claim 1.
* * * * *